(12) United States Patent
Verbiest

(10) Patent No.: US 10,605,751 B2
(45) Date of Patent: Mar. 31, 2020

(54) SYSTEM AND METHOD FOR DETERMINING A QUANTITY OF MAGNETIC PARTICLES

(71) Applicant: PEPRIC NV, Leuven (BE)

(72) Inventor: Joeri Verbiest, Duffel (BE)

(73) Assignee: PEPRIC NV, Leuven (BE)

(*) Notice: Subject to any disclaimer, the term of this patent is extended or adjusted under 35 U.S.C. 154(b) by 27 days.

(21) Appl. No.: 15/549,466

(22) PCT Filed: Feb. 8, 2016

(86) PCT No.: PCT/EP2016/052625
§ 371 (c)(1),
(2) Date: Aug. 8, 2017

(87) PCT Pub. No.: WO2016/128353
PCT Pub. Date: Aug. 18, 2016

(65) Prior Publication Data
US 2018/0031500 A1    Feb. 1, 2018

(30) Foreign Application Priority Data

Feb. 9, 2015 (EP) .................................... 15154399

(51) Int. Cl.
*G01V 3/00* (2006.01)
*G01N 24/10* (2006.01)
(Continued)

(52) U.S. Cl.
CPC .......... *G01N 24/10* (2013.01); *G01R 33/281* (2013.01); *G01R 33/60* (2013.01)

(58) Field of Classification Search
CPC .... G01R 33/60; G01R 33/441; G01R 33/345; G01N 24/10; G01N 24/08
(Continued)

(56) References Cited

U.S. PATENT DOCUMENTS 2,859,403 A    11/1958   Kirchner et al.
7,106,059 B2   9/2006    Takasugi et al.
(Continued)

FOREIGN PATENT DOCUMENTS

JP    2005326397 A    11/2005
JP    2012504247 A    2/2012
(Continued)

OTHER PUBLICATIONS

Anderson, "Applications of Modulation Techniques to High Resolution Nuclear Magnetic Resonance Spectrometers", The Review of Scientific Instruments vol. 33, No. 11, Nov. 1962, pp. 1160-1166.
(Continued)

*Primary Examiner* — Walter L Lindsay, Jr.
*Assistant Examiner* — Frederick Wenderoth
(74) *Attorney, Agent, or Firm* — Workman Nydegger

(57) ABSTRACT

A quantification of a particular element comprised in magnetic particles enclosed in a volume involves applying a first time-varying magnetic field to the volume, having a first magnitude and a first frequency and applying a second time varying magnetic field, not parallel with the first magnetic field for causing precession of the magnetized particles. The second magnetic field is an RF field having a second frequency equal to the Larmor-frequency of the particular element. Thereafter the resultant magnetization originating from the volume and modulated by the time-varying field is measured, and at least one frequency component of the resultant magnetization is determined. A power and/or voltage of the at least one frequency component is calculated and a quantity of the magnetic particles enclosed in the volume is determined based thereon.

17 Claims, 14 Drawing Sheets

(51) Int. Cl.
*G01R 33/28* (2006.01)
*G01R 33/60* (2006.01)

(58) Field of Classification Search
USPC .......................................................... 324/316
See application file for complete search history.

(56) References Cited

U.S. PATENT DOCUMENTS

| | | | |
|---|---|---|---|
| 8,816,685 B2 | 8/2014 | Vaes et al. | |
| 9,551,773 B2 | 1/2017 | Vaes et al. | |
| 2001/0028247 A1 | 10/2001 | King et al. | |
| 2003/0232084 A1* | 12/2003 | Groman | A61K 49/1863 424/486 |
| 2005/0053250 A1* | 3/2005 | Jonkman | H04R 25/30 381/312 |
| 2005/0237058 A1 | 10/2005 | Takasugi et al. | |
| 2007/0155024 A1* | 7/2007 | Miethe | G01N 27/745 436/524 |
| 2012/0049847 A1 | 3/2012 | Vaes et al. | |
| 2012/0126800 A1* | 5/2012 | Vernickel | A61B 5/05 324/234 |
| 2014/0009159 A1 | 1/2014 | Vaes et al. | |
| 2015/0268369 A1* | 9/2015 | Dodds | G01V 3/10 324/334 |

FOREIGN PATENT DOCUMENTS

| | | | |
|---|---|---|---|
| JP | 2014508947 A | 4/2014 | |
| RU | 2415433 C2 | 3/2011 | |

OTHER PUBLICATIONS

Chevion et al., "High Resolution EPR Studies of the Fine Structure of Heme Proteins. Third Harmonic Detection Approach", Biochimica et Biophysica Acta vol. 490, No. 2, Feb. 22, 1977, pp. 272-278.

Coene et al., "Quantitative Estimation of Magnetic Nanoparticle Distributions in One Dimension Using Low-Frequency Continuous Wave Electron Paramagnetic Resonance", Journal of Physics D: Applied Physics vol. 46, No. 24, Jun. 19, 2013, pp. 1-10.

European Search Report From EP Application No. 15154399.8, dated Apr. 20, 2015.

Fedin et al., "Absorption Line CW EPR Using an Amplitude Modulated Longitudinal Field", Journal of Magnetic Resonance vol. 171, 2004, pp. 80-89.

Gamarra et al., "Ferromagnetic Resonance for the Quantification of Superparamagnetic Iron Oxide Nanoparticles in Biological Materials", International Journal of Nanomedicine vol. 5, Mar. 24, 2010, pp. 203-211.

Gleich et al., "Tomographic Imaging Using the Nonlinear Response of Magnetic Particles", Nature vol. 435, Jun. 30, 2005, pp. 1214-1217.

Haworth et al., "The Use of Modulation in Magnetic Resonance", Progress in Nuclear Magnetic Resonance Spectroscopy vol. 1, Jan. 1, 1966, pp. 1-14.

International Search Report From PCT Application No. PCT/EP2016/052625, dated May 18, 2016.

Russian Office Action from RU Application No. 2017131335/28(054806), dated Jun. 4, 2019.

Japanese Office Action from corresponding JP Application No. 2017-541838, dated Dec. 3, 2019.

* cited by examiner

SYSTEM AND METHOD FOR DETERMINING A QUANTITY OF MAGNETIC PARTICLES

FIELD OF THE INVENTION

The invention relates in general to the field of characterization of magnetic particles, e.g. paramagnetic particles. More in particular, the invention relates to a system and a method for determining a quantity of magnetic particles present in a volume, as well as to imaging methods based thereon.

BACKGROUND OF THE INVENTION

Electron paramagnetic resonance (EPR) allows spectroscopic analysis of substances based on physical concepts analogous to those used in nuclear magnetic resonance (NMR). While NMR allows analysis of substances containing nuclides with non-zero spin, EPR is only applicable to substances containing chemical agents that possess at least one unpaired electron. NMR proves particularly useful in the analysis of substances comprising hydrogen atoms, which are abundantly present in water and hydrocarbons. Furthermore, Magnetic Resonance Imaging (MRI), an imaging technique based on NMR, is a valuable tool in medical diagnosis, due to the subtle contrasts caused by water density and complex spin-spin and spin-lattice interactions in different tissues.

EPR, on the other hand, has found less application in the past because all electrons in most stable chemical compounds are paired. However, the strength of EPR lies in its high specificity. EPR can readily be used for detection and imaging of free radicals in tissues, but the development of specific spin-labeled biological tracer molecules has spawned opportunities for the usage of EPR, and particularly the usage of EPR-based imaging techniques, for analysis of diverse physiological functions in biology and medicine. This opens the way for new tracers, specific to biological mechanisms that can't be studied by conventional means, and for alternatives to tracers used in nuclear medicine, without the implied radiation exposure caused by radionuclides.

EPR typically uses DC magnetic fields of 5 mT to 1.25 T or higher to cause magnetic polarization of particles with non-zero electron spin. Narrow-band radio-frequent waves are used to disturb the magnetization and cause resonance. The frequency at which resonance occurs, referred to as the Larmor precession frequency, is dependent on the applied magnetic field strength and specific material properties, and can range from 200 MHz for low field strengths to 35 GHz or higher for strong fields. The low-field (<30 mT) low-frequency (<1 GHz) region is particularly of interest for applications in biology and medicine because of diminished dielectric loss in tissues.

Quantification of the amount of magnetic, e.g. paramagnetic, particles using EPR signals can be performed directly on the EPR signal obtained using conventional EPR measurements. Nevertheless, in order to deal with a wide range of concentrations and to perform accurate quantification, there is still room for improvement.

SUMMARY OF THE INVENTION

It is an object of embodiments of the present invention to provide a method and a system for quantifying magnetic particles, e.g. paramagnetic particles, in an object. It is an advantage of embodiments of the present invention that methods and systems are provided for accurately quantifying magnetic particles, e.g. paramagnetic particles, in an object based on electron paramagnetic resonance (EPR) measurements, for a wide range of concentrations of magnetic particles, e.g. paramagnetic particles. It is an advantage of embodiments of the present invention making use of iron based magnetic particles, e.g. paramagnetic particles, in a given medium and volume, that accurate determination of the quantity can be performed. It is an advantage of embodiments of the present invention that use can be made of particles that are compatible with a large number of applications, both in vivo as for characterization of non-living objects.

It is an advantage of embodiments according to the present invention that fast imaging and/or volumetric imaging can be obtained using EPR based imaging techniques for detecting paramagnetic resonance of magnetic particles, e.g. paramagnetic particles, and this in an accurate and efficient manner.

This objective is accomplished by a method and device according to embodiments of the present invention.

The present invention relates to a method of determining a quantity of magnetic particles, e.g. paramagnetic particles, enclosed in a volume, the method comprising the steps of:

a) applying a first magnetic field ($B_0$) to said volume for magnetizing said magnetic particles, e.g. paramagnetic particles, the first magnetic field ($B_0$) being a time-varying field having a first magnitude and a first frequency ($f_{B0}$);

b) simultaneously applying to said volume a second magnetic field ($B_1$) not parallel to the first magnetic field ($B_0$) for causing precession of the magnetized particles, the second magnetic field being an RF field having a second frequency ($f_{B1}$) chosen substantially equal to the Larmor-frequency ($f_L$) of said particular element when exposed to the first magnetic field ($B_0$);

c) measuring the resultant magnetization (M) originating from the volume, the resultant magnetization (M) being modulated by the time-varying field;

d) determining at least one frequency component $f_{B1} \pm nf_{B0}$, n=1,3,5, . . . (i.e. n equals an odd value), of the resultant magnetization, and e) calculating a power and/or respectively voltage of the at least one frequency component $f_{B1} \pm nf_{B0}$, n=1,3, 5, . . . (i.e. n equals an odd value) of the resultant magnetization and determining from said power and/or voltage a quantity of the magnetic particles, e.g. paramagnetic particles, enclosed in the volume.

The modulation of the resultant magnetization may be an amplitude modulation by the time-varying field, but also may be any another type of modulation by the time-varying field.

The "quantity" can be expressed as a number of atoms, number of cells, or as a mass or as a concentration (in said volume), or in other ways.

It is an advantage of embodiments of the present invention using EPR that it provides a relatively high signal which can be reliably detected. It is an advantage of embodiments of the present invention that by making the transmission side and receiving side not parallel, more amplification can be applied in the respective parts.

It is an advantage of embodiment of the present invention using a modulated signal, in that it provides a spectrum with specific spectral components, from which said quantity can be derived. One advantageous example of modulation is amplitude modulation which can be easily implemented in embodiments of the present invention.

It is an advantage of embodiments of methods according to the present invention in that it is extremely sensitive over several orders of magnitude. It allows for example to determine a mass in the range down to 1 nanogram (ng) or lower, provided noise contributions of the different electronic components in the system and the environment can be accurately controlled. In some embodiments, the mass that can be detected is at least in the range of 9 ng to 4500 µg in a volume of for example about 30 to about 150 µl.

The magnetic particles may for example be Fe2O3 or Fe3O4, for which the electron paramagnetic behavior is known to the person skilled in the art. Such types of particles also are widely applicable, e.g. in characterization experiments as well as in medical applications. It is an advantage of embodiments of the present invention in that it allows the quantity to be accurately determined, irrespective of the size or shape of the particles, (e.g. nanoparticles having an average diameter ranging from 20 nm to 500 nm).

In a specific example, the paramagnetic particle is iron related, the first frequency is about 200 Hz, the magnitude of the first magnetic field is about 10.7 mT peak, and the second frequency (Larmor frequency) is about 300 MHz.

It is an advantage of embodiments of the present invention that no complete saturation is required. Compared to reference B. Gleich and J. Weizenecker. Tomographic imaging using the nonlinear response of magnetic particles. Nature, 435:1214-1217, 2005, where saturation is needed.

Determining at least one frequency component, $f_{B1} \pm nf_{B0}$, n=1,3,5, . . . (i.e. n equals an odd value) of the resultant magnetization may comprise determining a frequency spectrum of the resultant magnetization.

Determining at least one frequency component, $f_{B1} \pm nf_{B0}$, n=1,3,5, . . . (i.e. n equals an odd value), may comprise determining at least one frequency component at a frequency equal to the second frequency, $f_{B1}$, minus the first frequency, $f_{B0}$ (i.e. $f_{B1} - nf_{B0}$, with n=1, 3, 5, . . . , i.e. n equals an odd value.) or at a frequency equal to the second frequency, $f_{B1}$ plus the first frequency, $f_{B0}$ (i.e. $f_{B1} + nf_{B0}$, with n=1, 3, 5, . . . , i.e. n equals an odd value).

The frequencies $f_{B1} + nf_{B0}$ is also known as the "upper-side-band", the frequencies $f_{B1} - nf_{B0}$ is also known as the "lower side-band". These frequencies correspond to the first upper side-band and to the first lower side-band of the modulated waveform.

Determining from said power and/or voltage a quantity of the magnetic particles, e.g. paramagnetic particles enclosed in the volume may comprise determining a quantity based on a linear relationship between the power and/or voltage of said at least one spectral component and the mass of said magnetic particles, e.g. paramagnetic particles.

Determining from said power and/or voltage a quantity of the magnetic particles, e.g. paramagnetic particles, enclosed in the volume may comprise comparing said power and/or voltage with a reference power determined for a known quantity of said magnetic particles, e.g. paramagnetic particles.

The reference value is typically a value obtained by calibration using a sample volume with a known quantity of said element. Such a calibration may be performed at the time of measurement of the unknown sample but also may be a stored calibration measurement of which the result can be re-used for a plurality of further measurements.

The time varying first magnetic field may be a periodic time varying field.

The time varying first magnetic field may have a sinusoidal waveform.

The time varying second magnetic field may be a periodic time varying field.

The time varying second magnetic field may have a sinusoidal waveform.

The frequency of the first magnetic field, $B_0$, can be almost DC to frequencies up to a several kHz. For example, the frequency of the first magnetic field can be a frequency in the range of 10 Hz to 30000 Hz, preferably in the range of 70 Hz to 400 Hz, for example about 200 Hz.

The frequency of the second magnetic field, $B_1$, can be almost few MHz to frequencies up to a several MHz. For example, the frequency of the second magnetic field can be a frequency preferably in the range of 50 MHz to 1000 MHz, for example about 300 MHz.

It is an advantage of using the frequency $f_{B1} \pm nf_{B0}$, with n=1, which is much higher in power and/or voltage than the other frequencies $f_{B1} \pm nf_{B0}$, with n=3, 5, . . . . Compared to reference B. Gleich and J. Weizenecker. Tomographic imaging using the nonlinear response of magnetic particles. Nature, 435:1214-1217, 2005, where $nf_{B0}$, with n=3 is measured, which has a much lower power content than $nf_{B0}$, with n=1.

It is an advantage of using a one tone sinusoidal waveform for the first signal source and for the second signal source in that the spectral components are easily identifiable.

Finally, the requirement for building a measurement equipment is that the system itself, without the SUT (Sample Under Test) is an linear time invariant system. The SUT itself can be non-linear.

The present invention also relates to a system for determining a quantity of magnetic particles, e.g. paramagnetic particles, enclosed in a volume, the system comprising:
  a) a first signal source and a first magnetic field generating element for generating and applying a first magnetic field ($B_0$) to said volume for magnetizing said magnetic particles, e.g. paramagnetic particles, the first magnetic field ($B_0$) being a time-varying field having a first magnitude and a first frequency ($f_{B0}$);
  b) a second signal source and a second magnetic field generating element arranged for simultaneously applying to said volume a second magnetic field ($B_1$) not parallel with the first magnetic field ($B_0$), and having a frequency ($f_{B1}$) equal to the Larmor frequency ($f_L$) of said magnetic particles, e.g. paramagnetic particles for causing precession of the magnetized particles;
  c) a sensing element for measuring the resultant magnetization, the resultant magnetization (M) being modulated, for example amplitude modulated, by the time varying field;
  d) a processor programmed for determining at least one frequency component $f_{B1} \pm nf_{B0}$, n=1,3,5, . . . (i.e. n equals an odd value) of the resultant magnetization and further programmed for calculating a power and/or voltage of the at least one frequency component $f_{B1} \pm nf_{B0}$, n=1,3,5, . . . (i.e. n equals an odd value) of the resultant magnetization and for determining from said power and/or voltage a quantity of the magnetic particles, e.g. paramagnetic particles, enclosed in the volume.

It is an advantage of embodiments of the present invention that an accurate system for quantifying an amount of magnetic particles, e.g. paramagnetic particles, is provided, accurate over a wide range of concentrations of magnetic particles, e.g. paramagnetic particles.

It is to be noticed that for $B_0$, one can use a voltage controlled current source but also any other combination such as a voltage controlled voltage source, a current controlled current source, etc.

The processor furthermore may be programmed for determining the at least one frequency component at least at a frequency equal to the second frequency minus the first frequency ($f_{B1}-nf_{B0}$, with n=1,3,5, . . . , i.e n=odd value) or at a frequency equal to the second frequency plus the first frequency ($f_{B1}+nf_{B0}$, with n=1,3,5, . . . , i.e. n equals an odd value).

The system furthermore may comprise a memory for storing a reference power and/or voltage determined for a known quantity of said magnetic particles, e.g. paramagnetic particles and the processor being programmed for comparing the determined power and/or voltage with the reference power and/or voltage for determining a quantity of the magnetic particles, e.g. paramagnetic particles, enclosed in the volume.

The first signal source may be adapted for generating a periodically varying first magnetic field with a frequency in the range almost several Hz to several kHz The processor may comprise a means for calculating a frequency spectrum of the resultant magnetization.

The means for calculating a frequency spectrum may comprise a means for performing a (discrete) Fourier-transform, by using for example the Fast Fourier Transform or the Goertzel algorithm.

The processor may comprise a signal analyzer for determining a power and/or voltage of at least one frequency component $f_{B1}\pm nf_{B0}$, n=1,3,5, . . . (i.e. n equals an odd value) in the frequency spectrum of the resultant magnetization.

The processor may be part of a specific processing unit integrated in the system or may be a separate processing unit not integrated in the measurement system.

The present invention also relates to a method of imaging an object, the method comprising applying a method of determining a quantity of magnetic particles, e.g. paramagnetic particles, in a given volume as described above at a plurality of positions in the object, the determining being applied after administration of a dilution comprising said magnetic element, paramagnetic element to an object. Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
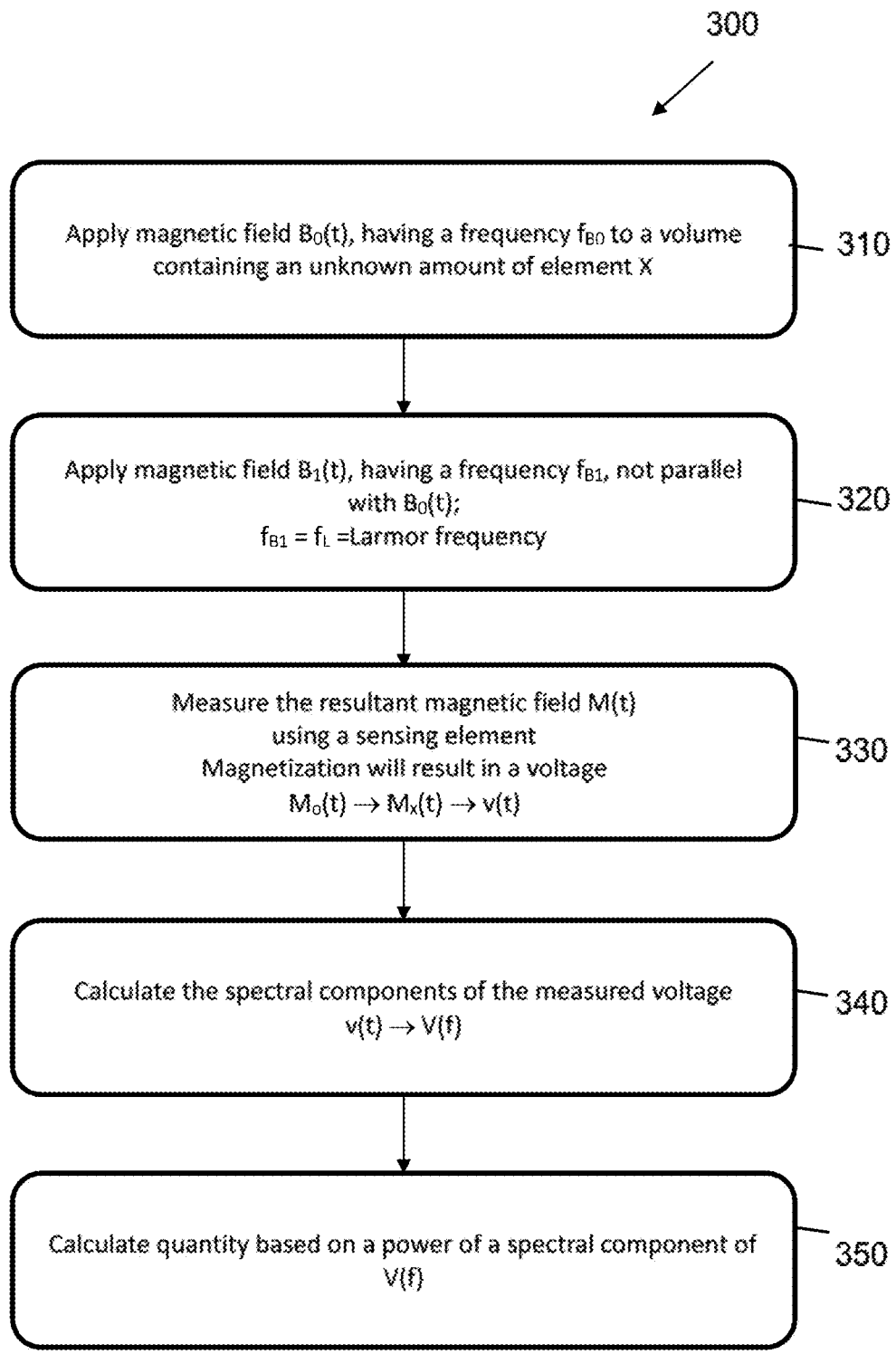
FIG. 1 is a flowchart illustrating an embodiment of a method according to the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description. In embodiments of the present invention, methods and systems are provided for gathering information about an object under test that includes particles presenting magnetic properties. These particles may be introduced in any suitable way such as for example by administering, by mixing, by pouring, etc. The particles presenting magnetic properties may for example be magnetic particles, magnetic nano-particles, target specific iron oxide particles and magnetic contrast agents, magnetic drug carriers particles for hyperthermia and thermo-ablation, pre-labeled cells, therapeutic cells and stem cells, and/or may be paramagnetic particles, superparamagnetic iron oxide (SPIO) and ultra-small iron oxide particles (USPIO).

Where in embodiments according to the present invention reference is made to a first magnetic field, reference is made to a magnetic field inducing orientation of the magnetization of the particles under study. Such an orienting magnetic field corresponds with the classic static magnetic field typically used for orienting magnetization of the particles under study in conventional EPR measurements. Nevertheless, as in embodiments of the present invention, the first magnetic field in the present example is not constant but is a time varying magnetic field.

Where in embodiments of the present invention reference is made to an RF field, at a frequency to generate electron paramagnetic resonance (EPR) in the object under test, reference is made to RF excitation typically having for example a frequency in the order of between 1 MHz and 1 GHz, for example a frequency in the order between 60 MHz and 500 MHz.

Where in embodiments of the present application the term nano-particles is used, reference is made to particles having a critical dimension, e.g. diameter, in the range of 1 nm to 1000 nm. For a number of embodiments, the size of the particles is further specified to be in a range as provided. The nano-particles or magnetic nano-particles may be single domain particles.

Where in embodiments according to the present invention reference is made to an object under study, such an object may be a non-living object or a living object. In some embodiments—the present invention not being limited thereto—the object may be a body of a living creature, such as for example an animal or human body. The object under study according to embodiments of the present invention are paramagnetic objects. Embodiments of the present invention can also be used for in-vitro testing, e.g. for the quantification of cells linked with the magnetic objects. Embodiments of the invention allow to quantify the magnetic objects with a high sensitivity and accuracy. Examples of applications include pure quantification to 3D imaging but are not limited thereto. Objects under study may be paramagnetic objects as of nature or may be made at least partially magnetic by adding, e.g. through administering, magnetic particles, such as magnetic nanoparticles, to the object. The administering step may be performed prior to application of the method according to embodiments of the present invention for detecting electron magnetic resonance of the object under study.

Where in method embodiments according to the present invention reference may be made to interaction between an object under study and one or more generated fields, the interaction between object and magnetic field or RF energy may be not part of the method. Method embodiments according to the present invention may thus encompass only the step of detecting upon interaction or the steps of generating the fields and detecting upon interaction.

Where in embodiments of the present invention reference is made to electron paramagnetic resonance in the framework of the present invention, reference is made to an EPR technique being a direct measurement technique that does not require further data analysis. In contrast to conventional EPR, in embodiments of the present invention, the EPR used, sometimes also referred to as pEPR or particle EPR, is a low field and low frequency EPR technique, where the perturbing electromagnetic field is applied in a continuous way (CW). As indicated the EPR technique used in embodiments of the present invention is a direct measurement not requiring further data analysis. This is in contrast with conventional EPR methods, wherein data is deduced from the absorption of the spectra, being the first derivative of absorbed power with respect to the applied field, from which a double integral is calculated to obtain a number proportional to the electron spin in the sample. In a first aspect, the present invention is related to determining a quantity (e.g. expressed in terms of mass, concentration or number of cells) of magnetic particles, such as for example paramagnetic particles, like e.g. paramagnetic nanoparticles, enclosed in a given volume. In one example, the particles may be iron oxide nanoparticle, although embodiments are not limited thereto.

The method according to embodiments of the first aspect comprises applying a first magnetic field ($B_0$) to said volume for magnetizing said magnetic particles, the first magnetic field ($B_0$) being a time-varying field having a first magnitude and a first frequency ($f_{B0}$). Simultaneously a second magnetic field ($B_1$), not parallel to the first magnetic field, is applied to said volume for causing precession of the magnetized particles, the second magnetic field being an RF field having a second frequency ($f_{B1}$) chosen substantially equal to the Larmor-frequency ($f_L$) of electron spins of the magnetic particles when exposed to the first magnetic field ($B_0$).

Whereas optimally the frequency of the second frequency ($f_{B1}$) is equal to the Larmor frequency, some deviation could be present. Nevertheless, the larger the difference, the less sensitive the technique becomes.

The RF field B1 varies in time with the Larmor frequency as indicated above. Advantageously, the second magnetic field ($B_1$) is substantially orthogonal or orthogonal to the first magnetic field ($B_0$). Such orthogonal orientation can be obtained in an electronic and or mechanical way.

According to embodiments of the present invention, the first frequency used can be significantly lower than in conventional EPR systems. The low frequency can for example be in the range 10 Hz to 30000 Hz for $f_{B0}$, and in the range 50 MHz to 1000 MHz for $f_{B1}$. In one example, the frequency used for $f_{B1}$ can for example be 300 MHz. It is an advantage of embodiments of the present invention that at these low frequencies, the attenuation inside tissues is less pronounced. The latter is advantageous if the technique is used with reference to in-vivo systems.

In some embodiments, the $B_0$ field frequency has an amplitude $v_1$ and a DC value $v_0$, the amplitude being given as:

$$v_{B0}(t) = v_0 + v_1 \cos(2\pi f_{B0} t)$$

In a typical setup the DC value is zero, $v_0=0$. Nevertheless, $v_0$ may be different from 0 and may be a DC value, e.g. 100 mV.

If a particle is brought in the $B_0$ field then precession is induced to the particle at Larmor frequency. Subsequently, a field $B_1$ is turned on, resulting in an increase of $\phi$, FIG. 4, which depends on the applied amplitude of $B_1$. This results in that we can measure $M_0$ using a sensing element, such as for example a coil. $B_1$ causes an increase in the transversal field.

The precession referred to is the precession of the magnetic moment with respect to the external magnetic field $B_0$ (electron spin).

The resultant magnetization (M) originating from the volume is measured whereby the resultant magnetization (M) is being modulated, for example amplitude modulated, by the time-varying field, $B_0$. The magnetization vector is the sum of all magnetic moments. The magnitude of the magnetization is correlated with the concentration of magnetic particles.

A discrete Fourier transform is performed on the voltage induced in the sensing element, representative for the magnetization. The induced voltage is given by:

$$u^P(t) = -\mu_0 \frac{d}{dt} \int_{object} p^R(r) \cdot M(r,t) d^3r = -\mu_0 \int_{object} p^R(r) \cdot \frac{\partial M(r,t)}{\partial t} d^3r$$

where $p^R(r)$ denotes the receive coil sensitivity, which contains all geometrical parameters of the sensing element, for example the sensing element may be a coil.

According to embodiments of the present invention, at least one frequency component, $f_{B1} \pm n f_{B0}$, n=1,3,5, . . . (i.e. n equals an odd value) of the induced voltage, which is a representative magnetization, is then determined, based on the discrete Fourier transform. Such at least one frequency component, $f_{B1} \pm n f_{B0}$, n=1,3,5, . . . (i.e. n equals an odd value) may also be a frequency spectrum, but embodiments are not limited thereto. From the at least one frequency component, $f_{B1} \pm n f_{B0}$, the power and or voltage is calculated and a quantity of the magnetic particles enclosed in the volume is determined based on the power.

Where in embodiments of the present invention reference is made to a quantity, reference is made to an amount of magnetic particles.

In advantageous embodiments of the present invention, the signal, obtained by a sensing element, is measured and discrete Fourier transform is applied. If the system is ideal and if there is no particle present, the signal is an unmodulated signal. If there is a particle present, the signal is a modulated signal. The modulated signal contains information of the magnetic particle. If a high speed ADC system is used with a sampling frequency, $f_s$, chosen so the Nyquist-Shannon sampling theorem is fulfilled, information can be extracted direct by performing a discrete Fourier transform. The outcome of the DFT results in a set of frequencies and a frequency component is used for determining information regarding to the quantity of the iron being present.

Alternatively, a demodulation technique can be used where an envelope signal will be extracted and the DFT on the envelope signal will be performed. The outcome of the DFT results in a set of frequencies and a frequency component is used for determining information regarding to the quantity of the iron being present. If the system is ideal one measures a sample without particles, the envelope is a DC value, if one measures a sample with particles, the envelope is the result of the Langevin and EPR contribution. The envelope signal contains information of the magnetic particle. Determining the envelope signal can be performed in a plurality of ways, for example using a product detector or envelope demodulator circuit or using digital signal processing techniques. Alternatively, when undersampling is performed, the envelope is the direct result of the measurements performed.

It is an advantage of embodiments of the present invention that no different orientations of the magnetic field are required, for example in comparison to US patent application US2014009159. Advantageously the complete signal is measured and there is only a need for a triggering at the start of the measurement to obtain accurate determination. With this method, there is no need for accurate triggering. The triggering may be a software or hardware trigger.

It is an advantage of embodiments of the present invention that the technique is less sensitive to EMI effects, since these can be filtered out by adding extra digital filtering before performing the DFT. The latter is possible because the complete information is available in the signal, for example in comparison to US patent application US2014009159.

In some embodiments, the RF field $B_1$ can be modulated in amplitude and/or in frequency. Since the amplitude of $B_0$ can vary, also the Larmor frequency can vary. Depending on this variation, the frequency of $B_1$ can vary, e.g. a variation between a few Hz to 300 MHz could be implemented. In some embodiments such a variation may for example be $$f_0 \pm \Delta f$$

with $\Delta f$ being equal to the bandwidth of the system.

The strength of the second magnetic field $B_1$ may be chosen according to the following procedure: The power of the $B_1$ signal is increased and simultaneously the amplitude of the spectral component is measured. The spectral component may be $f_{B1}+f_{B0}$ or $f_{IF}+f_{B0}$ in case of heterodyne based systems or $f_{B0}$ in case of an undersampling receiver. The optimal value for the strength of $B_1$ is the value where the power of the spectral component is maximal. Care is taken that the system is still operated as a linearly time invariant system.

Figure 3:
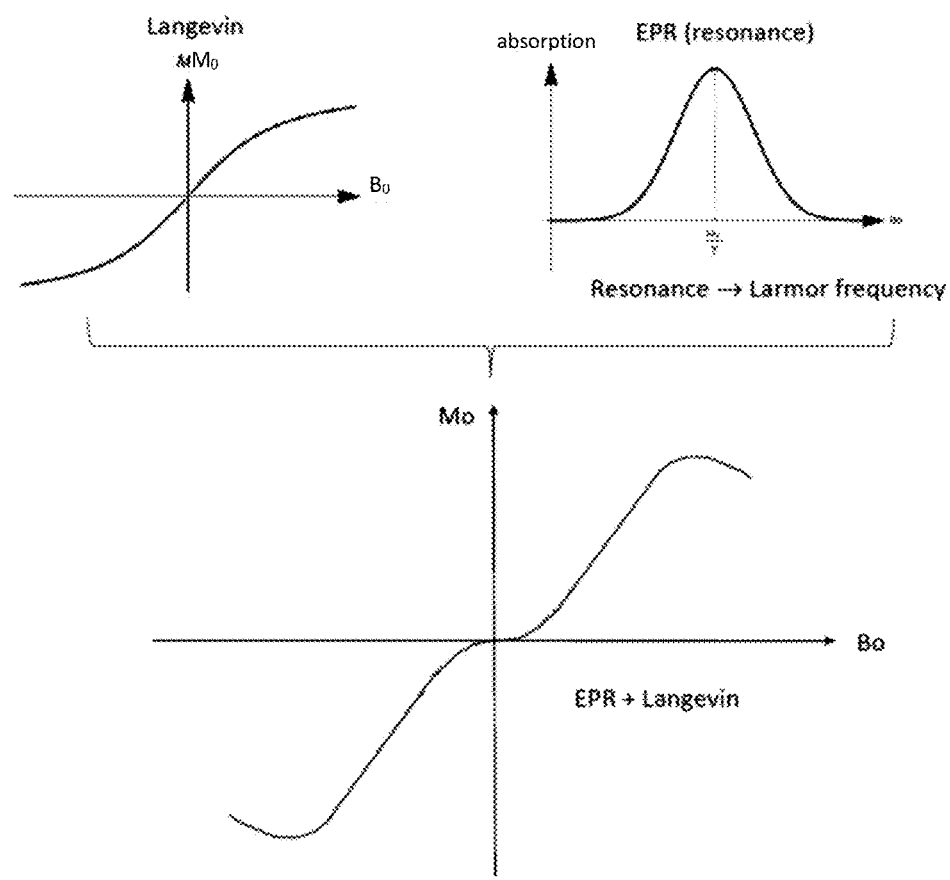
FIG. 3 shows a schematic representation of the behavior of superparamagnetic particles in a magnetic field as can be described by Langevin theory and electro-paramagnetic resonance effects, as can be used in embodiments of the present invention.

As indicated in FIG. 3, the concept of magnetic resonance is combined with the saturation effect (modeled using the Langevin function) of the particle magnetization.

Further features and advantages of embodiments of the present invention will be illustrated below, with reference to the drawings and to particular embodiments, the present invention not being limited thereto.

It is an advantage of embodiments of the present invention that the magnetic particle quantity is measured in a direct way and that not the endogenous particles, e.g. endogenous iron, i.e. those originating from within an organism, present in the biological tissue and fluid is measured. It thus is an advantage of embodiments that no additional measurements are required to extract endogenous particles.

It is an advantage of embodiments of the present invention that EPR can be done at a single temperature (i.e. there is no need to measure at different temperatures). The EPR measurement in embodiments of the present invention can be performed for example at room temperature or for example at about 37° C., i.e. a temperature close to the temperature of an animal or human body. Although not required a study of the particle effect as function of temperature still is possible.

The present invention is applicable for magnetic particles such as for example paramagnetic particles, including magnetic nano-particles, target specific iron oxide particles and magnetic contrast agents, magnetic drug carriers particles for hyperthermia and thermo-ablation, pre-labeled cells, therapeutic cells and stem cells, and/or may be paramagnetic particles, super-paramagnetic iron oxide (SPIO) and ultra-small iron oxide particles (USPIO).

It is an advantage of embodiments of the present invention that the EPR technique used does not make use of a cavity. This is an advantage to use the technique and system related to in-vivo systems.

The underlying principle of embodiments of the present invention will further be described below, whereby some mathematical considerations will be used which may explain the underlying principle. Nevertheless, embodiments of the present invention are not limited by these mathematical/theoretical considerations, the latter only provided as a possible way of explaining advantageous of methods and systems according to the present invention.

The principle of the measurement proposed by the present invention is based on the non-linear behavior of the magnetic particle and/or paramagnetic particle in an applied magnetic field $B_0$, described by the Langevin theory and the electro-paramagnetic resonance response to a magnetic RF-field.

Figure 4:
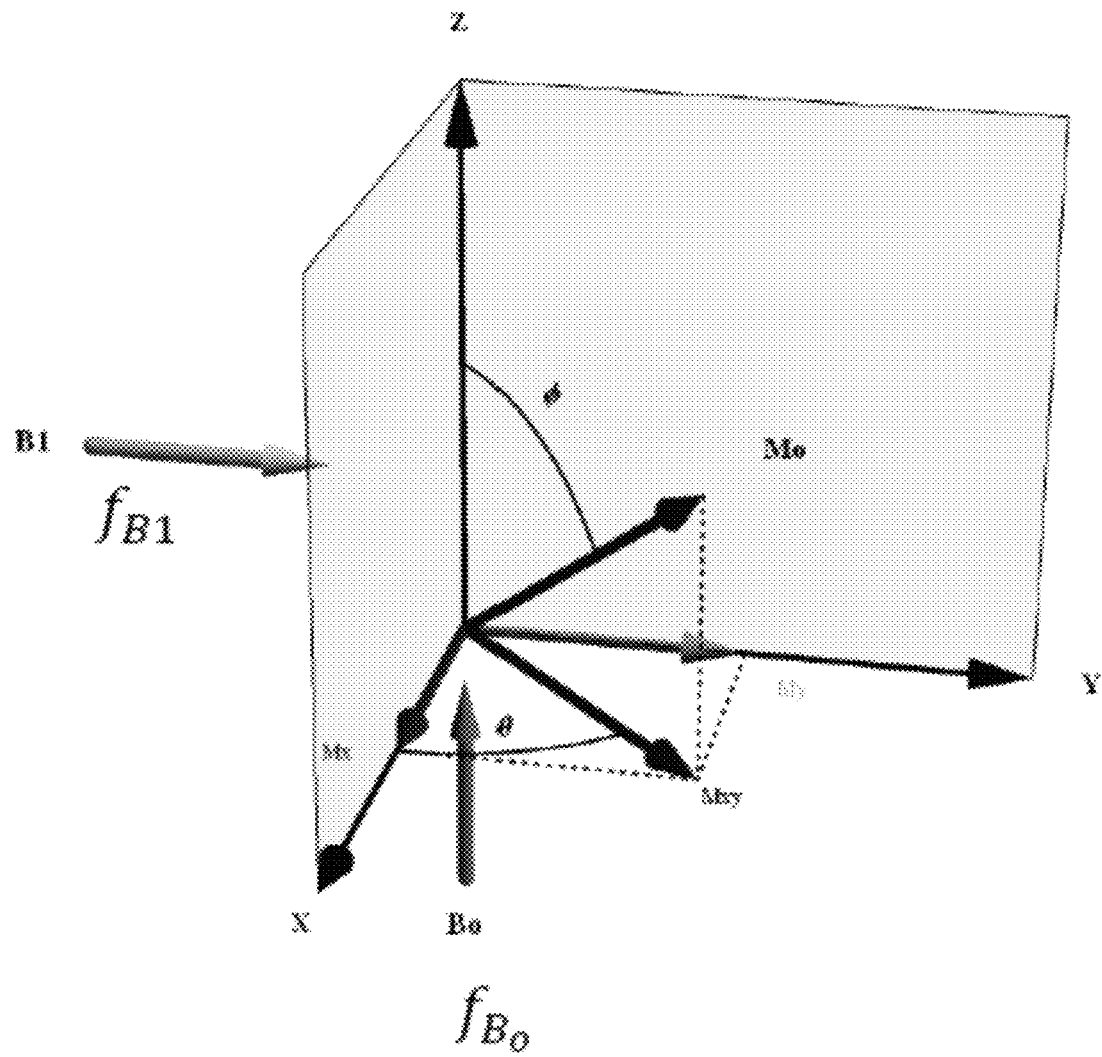
FIG. 4 illustrates the phenomenon of "precession", as used in embodiments according to the present invention.

If a magnetic particle and/or paramagnetic particle is placed in a static magnetic field $B_0$, it will align according to this field $B_0$. If the particle is then additionally excited by an RF-field $B_1(t)$, oriented orthogonal to the static field $B_0$, and having a frequency $f_{B1}$ (chosen equal or almost equal to the Larmor frequency $f_L$ of the particle of interest, e.g. Fe, in said static field $B_0$), a precession of the magnetic vector M of the iron particles about the axis of the magnetic field $B_0$ will occur. This phenomenon per se is known in the art, and is illustrated in FIG. 4, where the black vector M represents the magnetization vector M of the magnetic particle, paramagnetic particle, which vector rotates around the Z-axis at an angular velocity $\omega_L$, characteristic for each atom. Ideally the power applied to the $T_x$-coil is maximal so that the angle $\phi$ becomes 90°.

If however not a constant magnetic field $B_0$, but a time-varying magnetic field $B_0(t)$ is applied, for example a field $B_0(t)$ then not only the orientation but also the magnitude of the magnetization vector M will change. The change in magnitude can be described by a power series expansion (equation [1]) which is a combined result of the Langevin and the EPR resonance function, and can be expressed by:

$$y(t)=a_o+a_1x(t)+a_2[x(t)]^2+a_3[x(t)]^3+\ldots+a_n[x(t)]^n \quad [1]$$

with $x(t)=v_{B_o}(t)=v_o+v_1\cos(2\pi f_{B_o}t)$

The change in magnitude of the magnetization vector M can be observed (in the time-domain) using a sensing element as a modulated signal, and can be mathematically described by:

$$v_{R_x}(t)=v_{B_{1F}}\cos(2\pi f_{B_1}+\varphi)+y(t)\cos(2\pi f_{B_1}t) \quad [2]$$

With $v_{B_{1F}}\cos(2\pi f_{B_1}+\varphi)$ the feed-through signal which is an attenuated and phase shifted ($\phi$) version of the RF signal, $y(t)\cos(2\pi f_{B_1}t)$ is the modulation term, e.g. amplitude modulation term.

Figure 6:
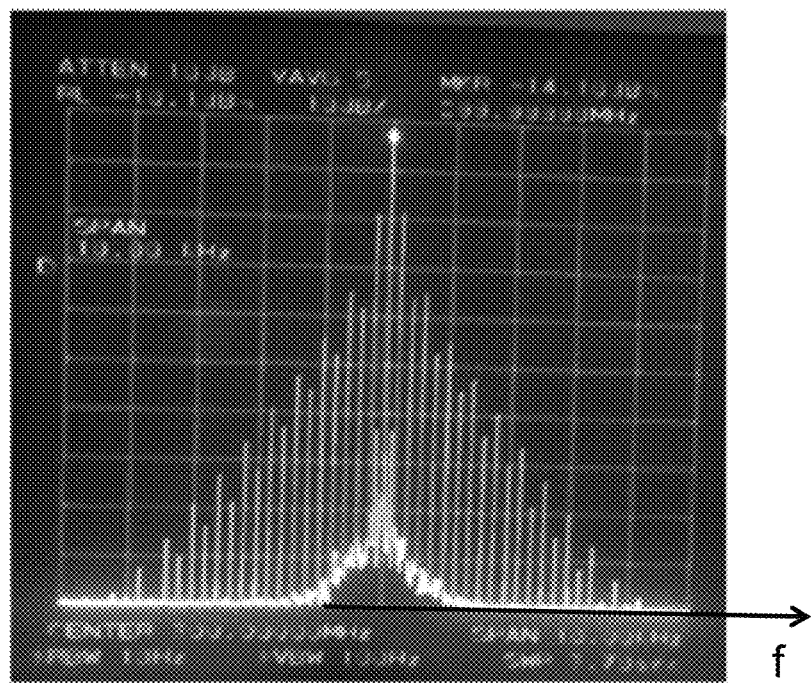
FIG. 6 shows a frequency spectrum (measured with a spectrum analyzer having a heterodyne receiver front end), as can be obtained using a method according to an embodiment of the present invention.

Equation [2] is an amplitude modulated signal in the time-domain, which has a frequency spectrum as shown in FIG. 6. The inventors shows that the power and/or voltage of the first spectral components of the first lower-side-band, LSB (at frequency $f_{B1}-f_{B0}$) and the power or voltage of the first spectral component of the first upper side-band, USB (at frequency $f_{B1}+f_{B0}$) is related to the quantity of the magnetic particle, paramagnetic iron oxide nanoparticles in a given medium and volume. Moreover the relationship is linear, i.e. in general the power and/or voltage of the uneven spectral components ($f_{B1} \pm n f_{B0}$, with n=1,3,5, . . . ) of the LSB or USB are proportional to the quantity of iron elements in the sample that was measured.

Next, an embodiment of a method and a system according to the present invention are described in some more detail.

Figure 2:
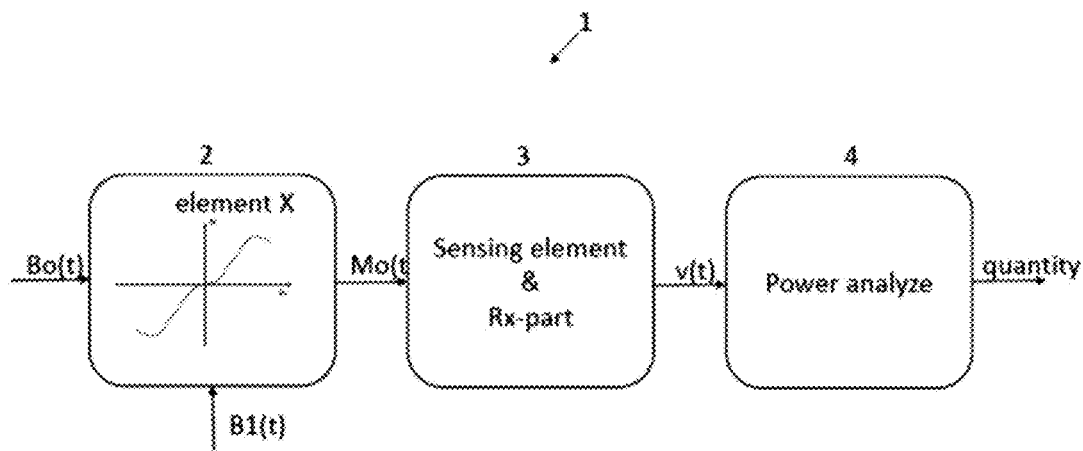
FIG. 2 is a schematic block-diagram of a system according to the present invention.

FIG. 1 shows a flow-chart of an embodiment of a method according to the present invention, and FIG. 2 shows a schematic block-diagram of a system according to an embodiment of the present invention. Assume that a volume 2 comprising an unknown amount of a particular paramagnetic particle (e.g. iron oxide) is provided, and that the amount of iron in the volume is to be determined. (The amount or quantity can be expressed as the mass, concentration, number of cells, or in other suitable ways).

Referring to FIGS. 1 and 2, in a first step 310, a first magnetic field $B_0(t)$ having a frequency $f_{B0}$ (for example about 200 Hz), and oriented in a first direction, is applied to the volume 2. The magnitude of the field may be for example 10.7 mT (for $f_{B1}$=300 MHz). According to embodiments of the present invention the first magnetic field thus is a time varying magnetic field. The frequency $f_{B0}$ can be in a range from several Hz to over the 100 kHz. Higher frequencies have an advantage because noise is in receivers mainly dominated by 1/f behavior, however this frequency may not become too high because particles has finite relaxation times, i.e. particles can only follow a variation up to a specific frequency. There is also a limitation which is related to the specific absorption rate (SAR), which becomes important in case of exposure of animals and humans. The SAR is proportional to the square of the field amplitude and frequency.

In a second step 320, a second magnetic field $B_1(t)$, oriented orthogonal to the field $B_0$, and having a frequency $f_{B1}$ substantially equal to the Larmor frequency of the particle of interest (in the example: iron) is simultaneously applied to the volume 2. The frequency $f_{B1}=f_L$ may be for example 300 MHz. By way of example, when Rienso® is used, the field strength may be much lower up to 7 mT in case of 300 MHz excitation. Due to the applied first and second magnetic field $B_0$ and $B_1$, the magnetic particle, e.g. paramagnetic particles, will show a magnetization M which is a combination of two effects: the first effect can be described by Langevin equations, the second effect can be described by EPR absorption. This is illustrated in FIG. 3. As can be seen from FIG. 3, the measured signal shows in a direct way the combination of the EPR and Langevin contributions. The technique and system also allows to measure hysteresis effects of the particles. The technique and system thus allows to extract a lot of information about the particle behavior.

In a third step 330 this magnetization signal M(t) is measured using a sensing element. The measured signal is modulated due to the time variable first magnetic field that is used.

In a fourth step 340 at least one frequency component ($f_{B1}+nf_{B0}$, with n=1) but optionally a full frequency spectrum ($f_{B1} \pm nf_{B0}$, with n=1,3,5, . . . ) of this signal is determined (e.g. calculated). The at least one frequency component may be determined for example by means of a spectrum analyzer or by other means capable of performing a (Discrete) Fourier-Transform such as for example a computer program or a suitably programmed Digital Signal Processor (DSP) or Field Programmable Gate Array (FPGA). An example of such a spectrum is shown in FIG. 6, showing a main peak at 300 MHz, and several smaller peaks on the left and on the right of the main peak (at distances which are multiples of 200 Hz in this example).

Finally, in a fifth step 350, the quantity of iron is calculated on the basis of a power and/or voltage of the at least one frequency component, $f_{B1}+nf_{B0}$, with n=1. In one example, the calculation may be based on the power of the first upper-sideband $P_{1\_USB}$ at $f_{B1}+f_{B0}$ and/or the power of the first lower sideband $P_{1\_LSB}$ at $f_{B1}-f_{B0}$ which is related to the mass of the magnetic nanoparticle and/or paramagnetic nanoparticle present in the volume 2. It is preferable to take $f_{B1}+f_{B0}$ or $f_{B1}-f_{B0}$ frequency component, there this has the maximum power content. Nevertheless, other frequency components also can be used, such as for example $f_{B1} \pm nf_{B0}$, with n=3.

The obtained result may for example be evaluated based on theoretically expected results, by comparing with a calibration method, using look up tables, using an algorithm, . . . . In some embodiments where a calibration is used, the power of at least one frequency component, e.g. the peaks at the $P_{1\_USB}$ and/or the $P_{1\_LSB}$ of a known sample, e.g. of a Rienso® A sample (further abbreviated as Rie A with 4500 µg Fe) may be used as a reference value. In such cases, the amount (e.g. quantity or mass or concentration) of magnetic particles, e.g. paramagnetic particles, present in an unknown specimen can be determined, as will become clear by the following experimental results.

Figure 17:
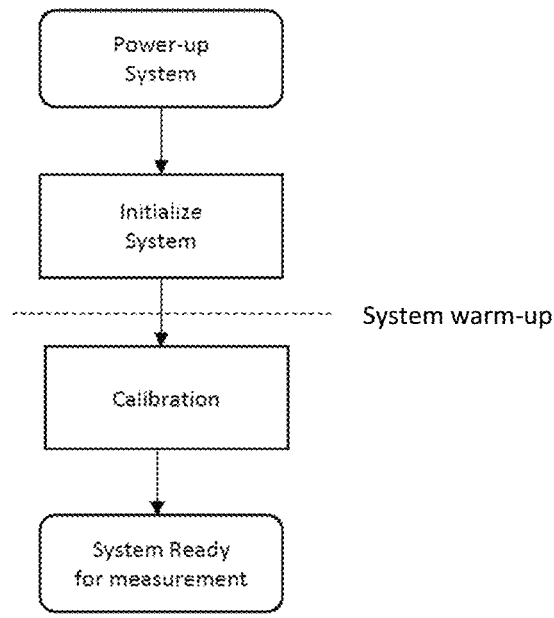
FIG. 17 illustrates an example of a method for calibrating the system, as can be used in an embodiment of the present invention.

In some embodiments of the present invention, the method comprises a calibration phase. Before starting a measurement, advantageously a start-up sequence can be performed including a calibration step, resulting in an optimum detection limit. An example of such a sequence is shown in FIG. 17, illustrating a power-up of the system, an initialization of the system, and after a system warm-up, a calibration phase thereafter resulting in a system ready for measurement.

During the initialization of the system, individual components are set to their correct values so the correct signal are applied where needed.

Figure 18:
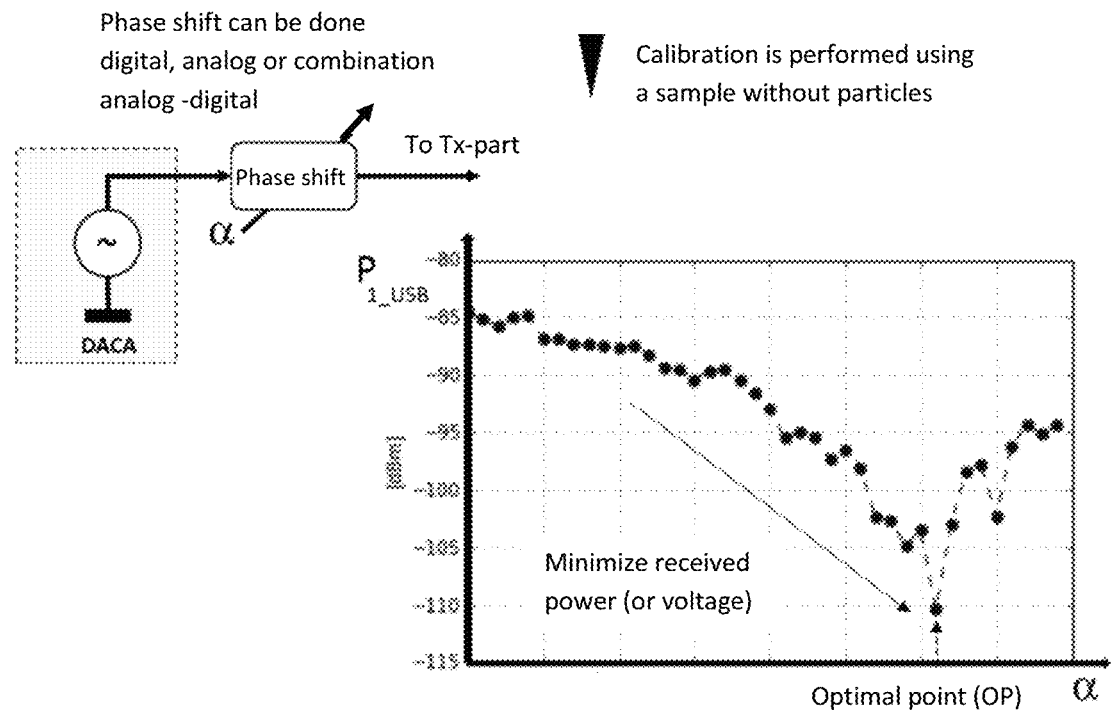
FIG. 18 illustrates an example of a phase shift calibration, as can be obtained using an embodiment of the present invention.

After the warm-up of the system, in the calibration step a sample without nano-particles is inserted in the sensing zone and the phase of $B_1$ is modified. This phase shift can be performed in a digital manner, an analog manner or a combination. The goal is to set an optimal point (OP) in such a way that received power or voltage at $P_{1\_USB}$ (or $P_{1\_LSB}$) is minimized, i.e. as close as possible to the noise floor of the system. An example of the phase optimization is shown in FIG. 18. This calibration step improves the sensitivity of the system (i.e. detection limit) and the accuracy and precision of the final result. This calibration step is especially relevant in a non-orthogonal coil system, i.e. where the $T_x$-, $R_x$-coil and the Helmholtz coil are not electrical orthogonal. It is to be noted that the optimal point is sensitive to (thermal) drift, to obtain the most accurate results thermal drift needs to be minimized and the calibration step needs to be repeated on a regular basis. Once the calibration is performed the system is ready for measurements.

In a second aspect, the present invention also relates to a system for determining a quantity of magnetic particle, e.g. paramagnetic particles, in an object. Such a system may be advantageously adapted for performing a method as described in the first aspect, but is not limited thereto. The system according to embodiments comprises a first signal source and a first magnetic field inducing element, e.g. a coil, for generating and applying a first magnetic field ($B_0$) to said volume for magnetizing said magnetic particles, e.g. paramagnetic particles, the first magnetic field ($B_0$) being a time-varying field having a first magnitude and a first frequency ($f_{B0}$). The system also comprises a second signal source and a second magnetic field inducing element, e.g.

coil, arranged for simultaneously applying to said volume a second magnetic field ($B_1$) orthogonal to the first magnetic field ($B_0$), and having a frequency $f_{B1}$ equal to the Larmor frequency ($f_L$) of said magnetic particles, e.g. paramagnetic particles, for causing precession of the magnetized particles. The system also comprises a measurement unit, e.g. a coil, for measuring the resultant magnetization, the resultant magnetization (M) being modulated by the time varying field, e.g. amplitude modulated. The system furthermore comprises a processor programmed for determining at least one frequency component, $f_{B1}+nf_{B0}$, with n=1 or $f_{B1}-nf_{B0}$, with n=1 of the resultant magnetization and further programmed for calculating a power of the at least one frequency component of the resultant magnetization and for determining from said power a quantity of the magnetic particles, e.g. paramagnetic particles, enclosed in the volume. The measurement unit may be any suitable sensor allowing measurement of magnetization.

Figure 11:
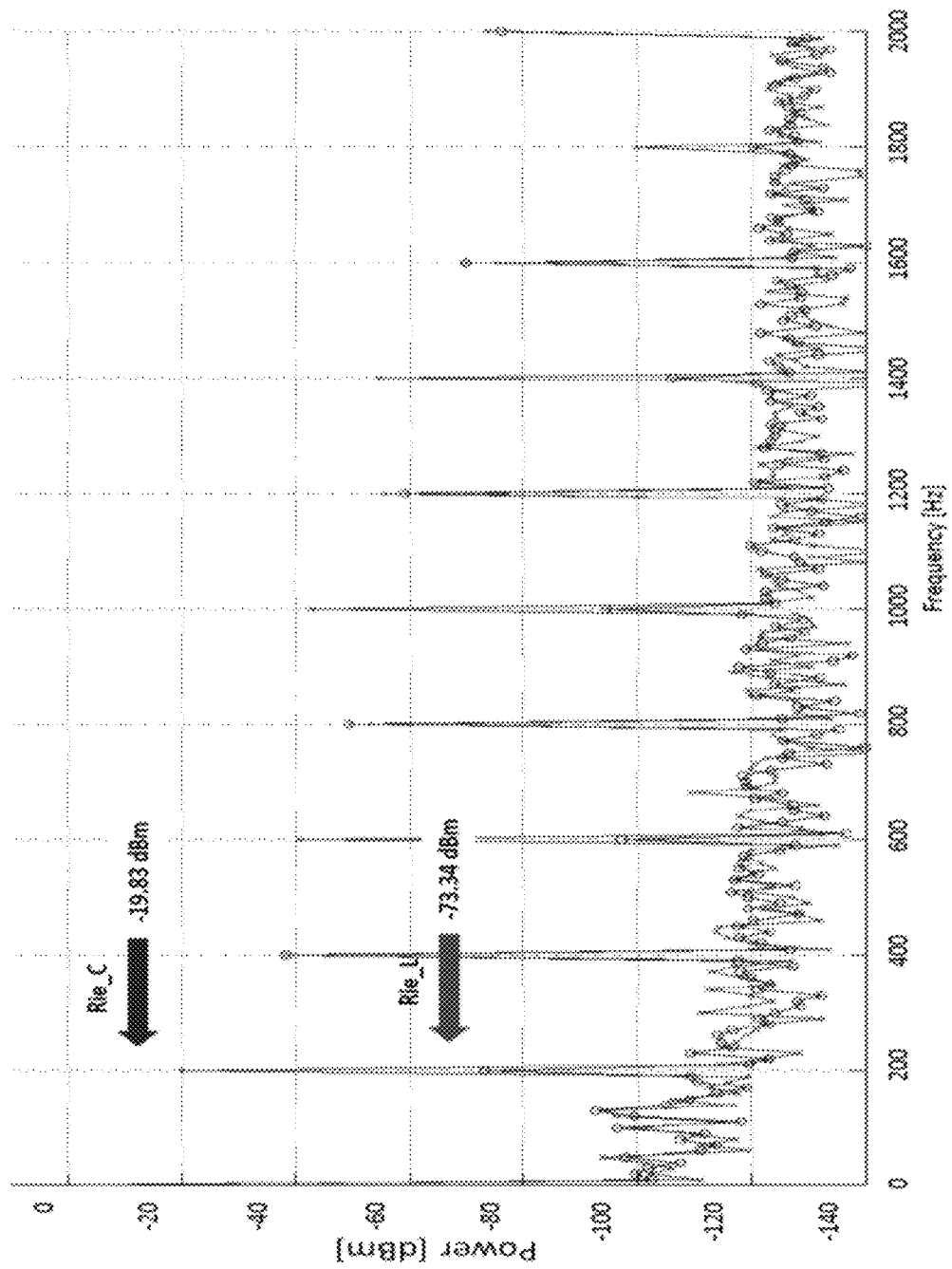
FIG. 11 shows a frequency spectrum calculated using FFT for a signal measured using undersampling according to an embodiment of the present invention.

FIG. 11 shows a frequency spectrum calculated using a Fast Fourier Transform. For the present example the software tool Matlab 2012b were used. The signal was measured using an undersampling or bandpass sampling approach whereby an ADC sampling at a rate 75 MSPS was used. In the particular example a on the shelf solution for the DAC/ADC FMC card (FMC176) and a high-performance with advanced Digital Signal Processing and multiple I/O options (PC720) where used. The specific cables used give rise to specific losses, resulting in possible small differences for different measurements, as can be seen in the experiment shown in FIG. 11 and the experiment described by table 2.

Figure 12:
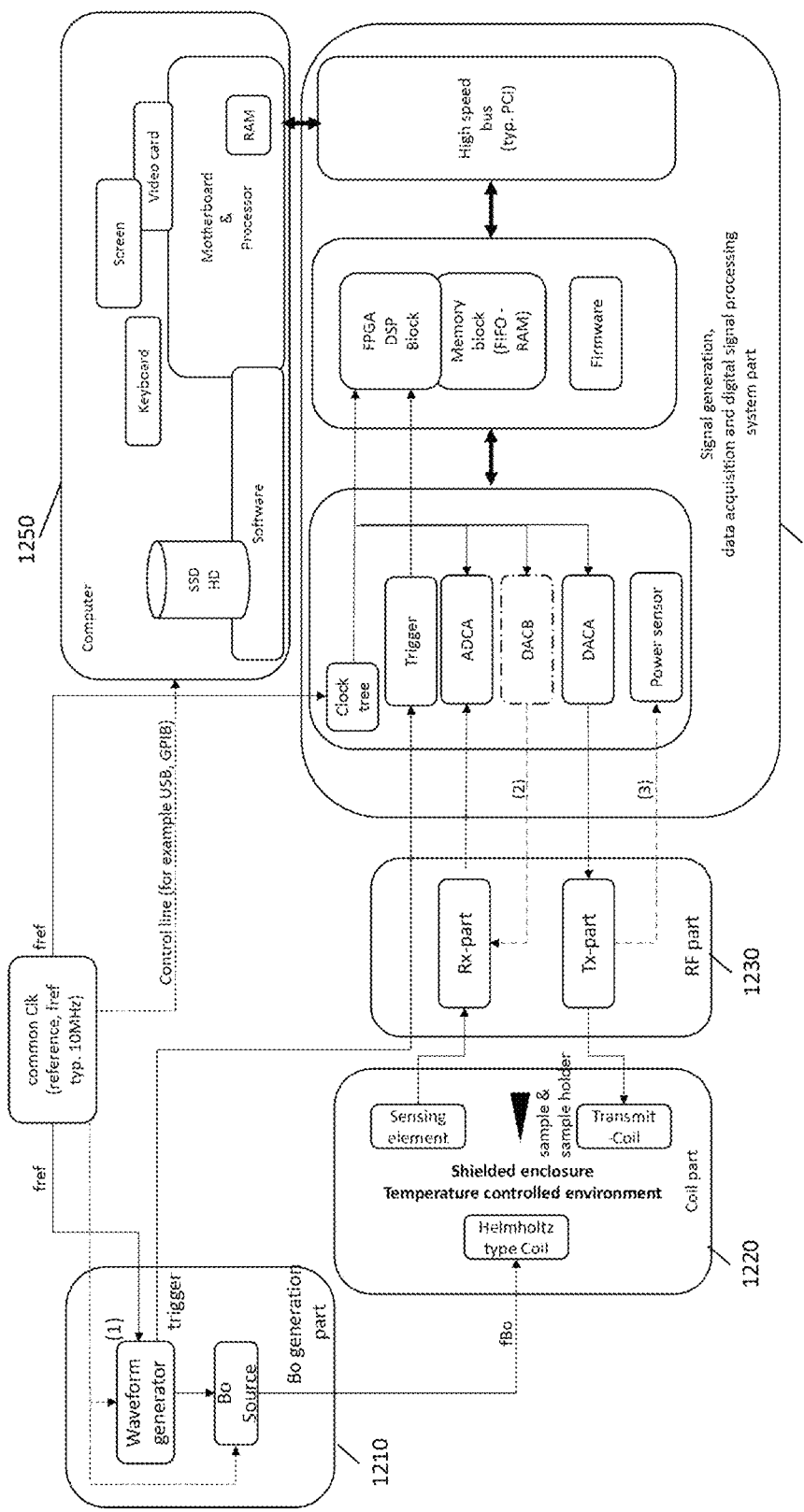
FIG. 12 shows a system for performing methods according to embodiments of the present invention.

FIG. 12 shows the system used for measuring the frequency spectrum shown in FIG. 11. The time required for taking measurements depends on the particle concentration, whereby lower concentrations require a longer measurement time. In the experiments performed, a typical experiment measurement time was 25 to 60 seconds.

The exemplary system shown in FIG. 12 illustrates some standard and optional components of a system according to an embodiment of the present invention. The system comprises a magnetic field $B_0$ generation part 1210. Typically such part may comprise a waveform generator and a magnetic field $B_0$ source. The waveform generator may be provided with a common clock signal as a reference signal. The waveform generator can be a separate block or it can be part of the $B_0$ source. The system also comprises a coil part 1220, wherein a Helmholtz type coil is fed with a magnetic field signal from the $B_0$ generation part, a transmit coil is provided and a sensing element is provided. The sample holder and a sample are positioned therein. The coil part typically may be a shielded enclosure and may be configured to be a temperature controlled environment. The system also comprises an RF part 1230, wherein a transmission part for feeding the transmit coil and a receiver part for feeding the sensing element, is provided. The system furthermore comprises a signal processing part 1240 configured for signal generation, data acquisition and digital signal processing. The signal processing part 1240 typically may be fed with the same reference clock as the waveform generator. The signal processing part 1240 also may comprise a triggering element for linking the waveform generator signal with the obtained results. The signal processing part 1240 typically also comprises one or more analogue to digital convertors and/or digital to analogue converters. Furthermore an FPGA and/or digital signal processing block, a memory block with a FIFO-RAM and possible firmware. The signal processing part 1240 may comprise a power sensor for measuring the power for controlling and/or sweeping the applied power to the transmit coil. Via a bus, e.g. a high speed bus may be used for providing communication with a computing system. Such a computing system may provide conventional components such as a motherboard, a processor, a memory such as a random access memory. A solid state device memory or hard disk memory also may be provided. Other components such as an input device, like a keyboard, an output device, like a screen, and a video card also may be present.

Figure 13:
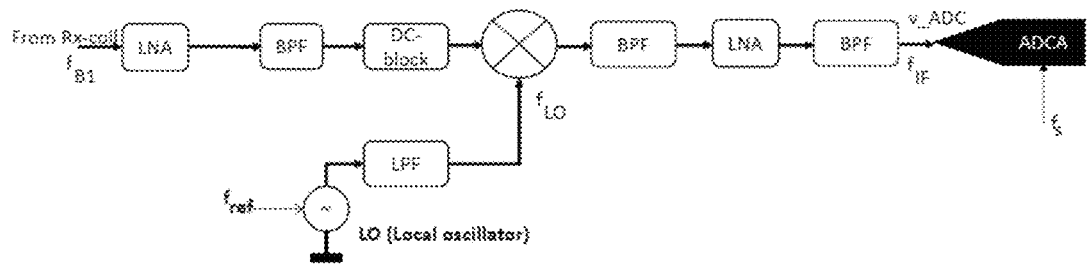
FIG. 13 shows a typical heterodyne based receiver part, as can be used in embodiments of the present invention.
Figure 14:
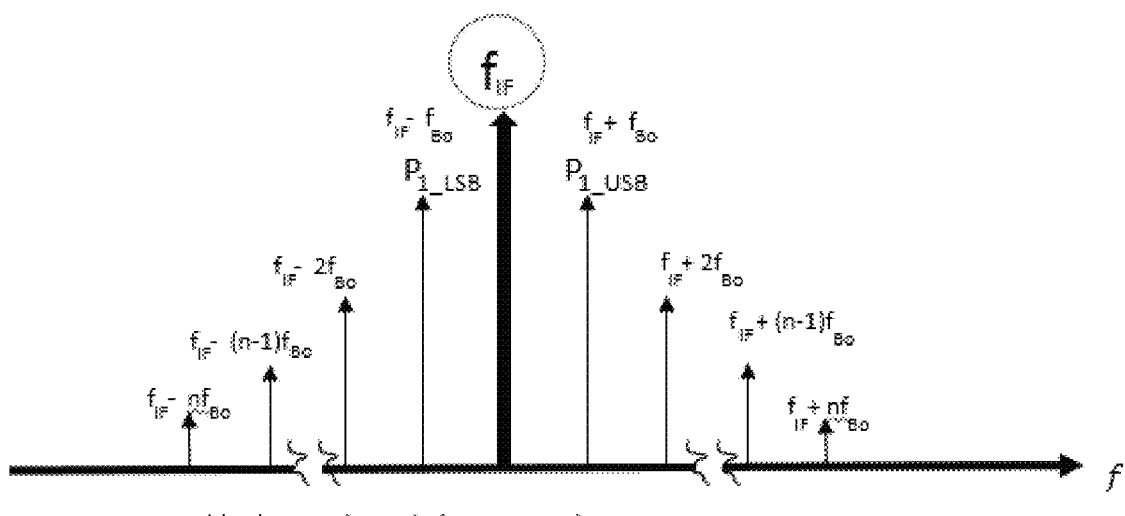
FIG. 14 illustrates a frequency spectrum corresponding with the heterodyne based receiver part of FIG. 13, as can be used in embodiments of the present invention.

In some embodiments of the present invention, the receiver part may be a heterodyne receiver part. In a heterodyne based receiver the signal at frequency $f_{B1}+nf_{B0}$ and $f_{LO}$ are mixed creating a sum frequency ($f_{B1}\pm nf_{B0}+f_{LO}$) and a different frequency ($f_{B1}\pm nf_{B0}-f_{LO}$), only one of the two are used, i.e. $f_{B1}\pm nf_{B0}-f_{LO}=f_{IF}\pm nf_{B0}$ ($f_{IF}$=intermediate frequency) and the other is filtered out. In a heterodyne based system the spectral components are down-converted around $f_{IF}$. The IF signal is digitized using a ADC (analog-to-digital converter). The ADC sampling frequency, $f_s$, is chosen so the Nyquist-Shannon sampling theorem is fulfilled, i.e. min. twice the upper cut-off frequency. An example of a heterodyne receiver is shown in FIG. 13 and a corresponding frequency spectrum is shown in FIG. 14.

Figure 15:
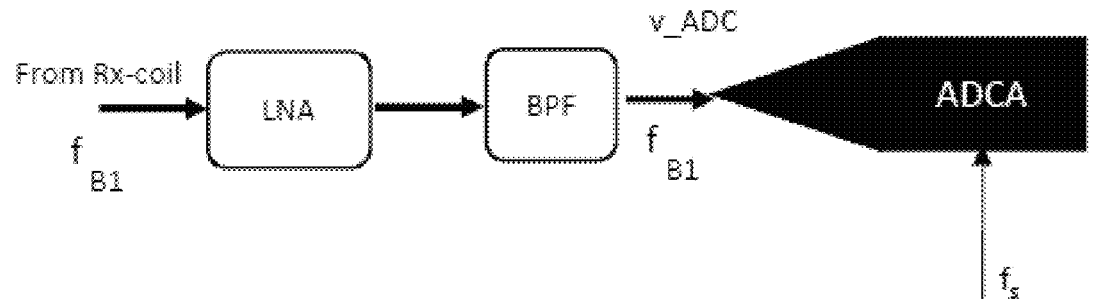
FIG. 15 illustrates a typical undersampling receiver part, as can be used in embodiments of the present invention.
Figure 16:
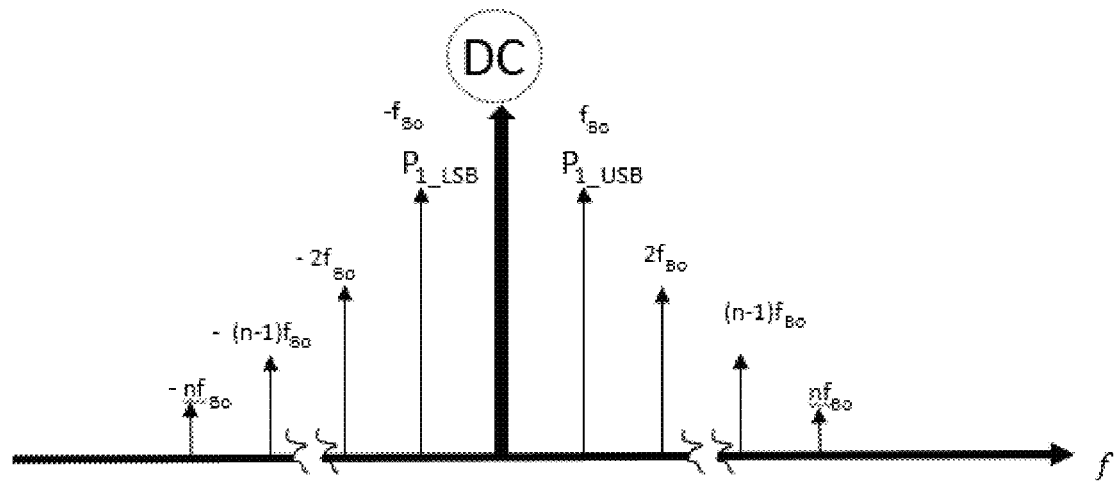
FIG. 16 illustrates a frequency spectrum corresponding with the undersampling receiver part of FIG. 15, as can be used in embodiments of the present invention.
Figure 19:
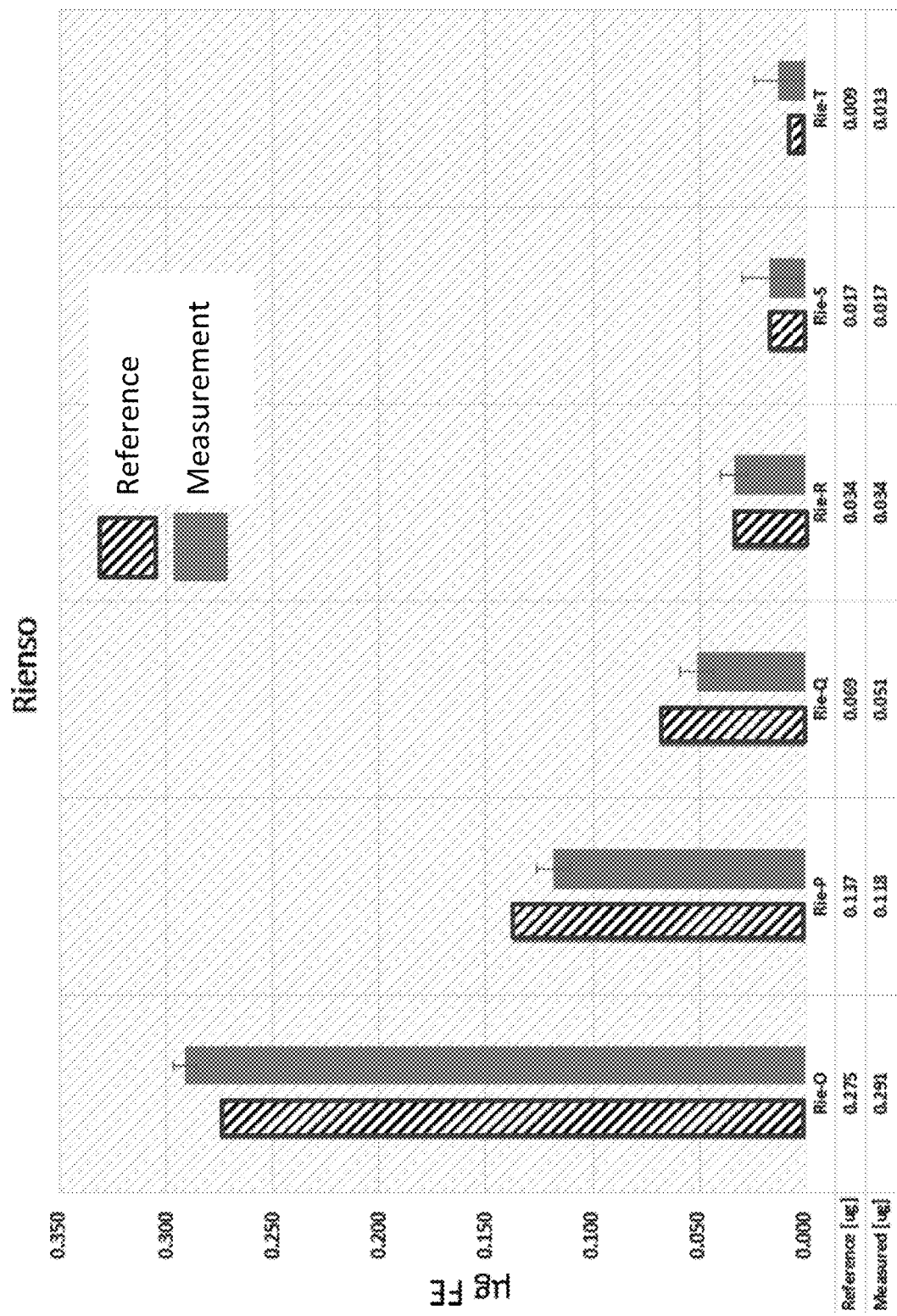
FIG. 19 shows the actual Fe content, and the content as determined by the undersampling method for Rienso® sample O (275 ng) to Rienso® Sample T (9 ng) using a system based on FIGS. 12 and 15, by measurement of P1_USB ($nf_{B0}$, with n=1), FIG. 16 and by performing the start-up sequence and calibration procedure as described in respectively FIG. 17 and FIG. 18.

In some embodiments of the present invention, the receiver part may be an undersampling system. In an undersampling system, the $B_1$ signal is digitized at a sample rate below the Nyquist rate. In case of the system described in the patent, the sampling rate is taken such that $f_s=f_{B1}/N$. A typical value for N=4, $f_s$=75 Msps. In this case $f_{B1}\pm nf_{B0}$ is down-converted to DC and the spectral components $\pm nf_{B0}$ around $f_{B1}$ are after down-conversion lying around the DC value. A narrow bandwidth band pass filter is used so that the harmonics of B1 are sufficient suppressed before applying the signal to the ADC. An example of an undersampling based receiver is shown in FIG. 15 and a corresponding frequency spectrum is shown in FIG. 16. FIG. 19 shows the measured quantity of iron using an undersampling based receiver.

Embodiments of present invention may comprise magnetic field gradient generators adapted for imaging and/or volumetric imaging purposes. Such embodiments may furthermore comprise a procession unit adapted for combining the detected signals in the form of image and/or volumetric image representations of the object under test.

By way of illustration, embodiments of the present invention not being limited thereby, in one example imaging could be performed by inducing a field gradient over the sample. For example in a 1-dimensional case, applying a field gradient (e.g. 0→10 mT) over the sample (e.g field of view of 2 cm), the spins will give a different response depending on their position (corresponding with the Langevin equation). Applying different field gradients (e.g. 0→5 mT, 10→0 mT, . . . , 0→-10 mT, -10→0 mT, 0→-5 mT) will result in a set of equations allowing resolving the concentrations at each of the individual positions. The latter can be extended to 2 or 3 dimensions. In another example, resonance condition is created only at one position, ±10 mT at one location and 0 mT at all the other locations.

Experiment

Figure 5:
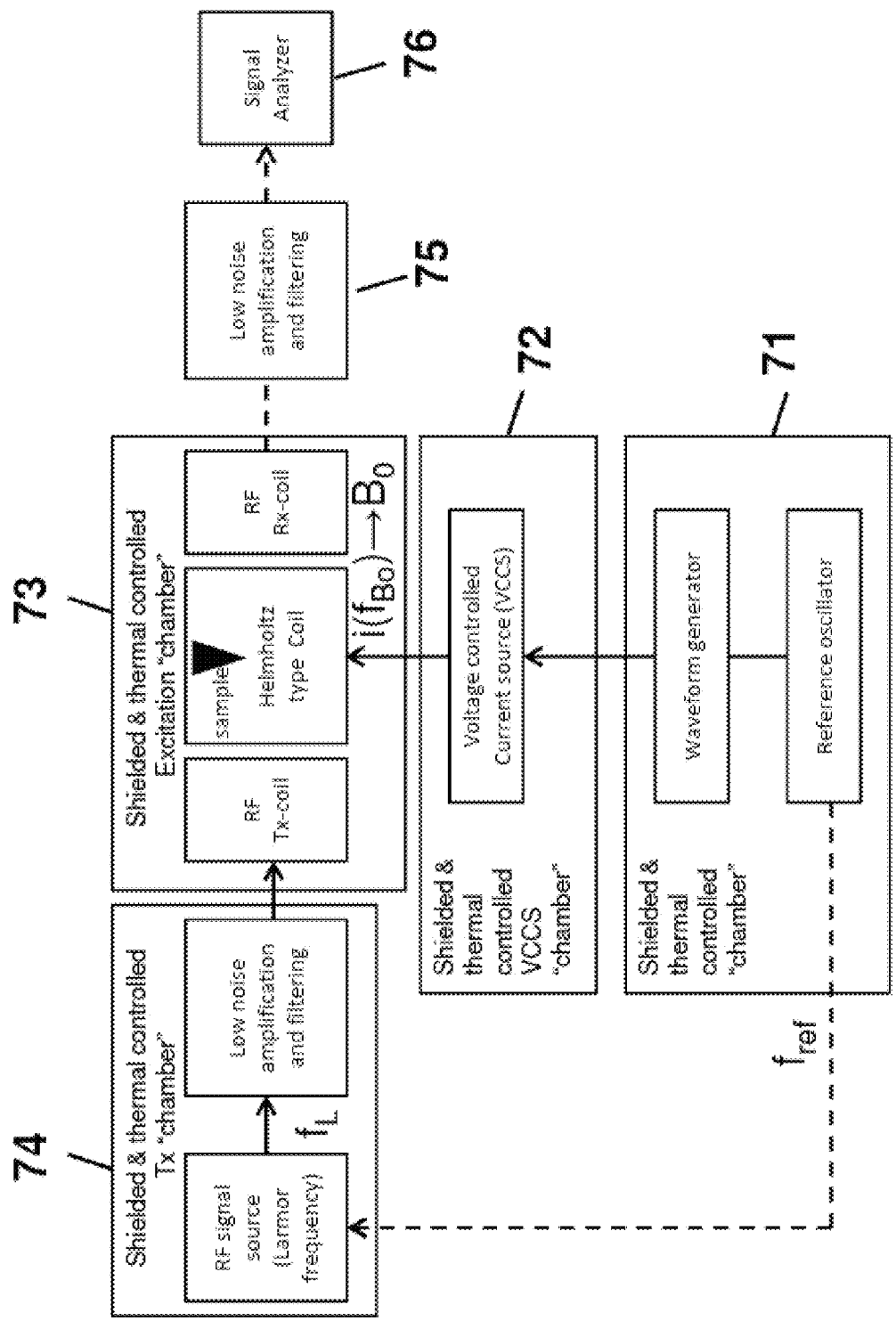
FIG. 5 shows an example of a typical setup as can be used in an embodiment of the present invention.

FIG. 5 describes an experimental setup as proof of the concept. A first shielded & thermal controlled chamber 71 contains a reference oscillator for generating a stable reference frequency ($f_{ref}$=typical 10 MHz). It is to be noticed that an asynchronous operation could also work. When asynchronous operation is used nevertheless, the system becomes sensitive to drift, i.e. drift between $B_0$-field and $B_1$-field and thermal drift. Asynchronous operation will result in less sensitivity so a preference to synchronous operation may be present. The $R_x$-coil can be oriented in any suitable orientation. Maximum sensitivity is obtained when the $R_x$-coil is oriented perpendicularly to the $T_x$-coil.

The same chamber 71 further contains a waveform generator for generating a stable sinusoidal voltage signal (in the example a one tone at $f_{B0}$=200 Hz). The stable reference frequency $f_{ref}$ is applied to an RF signal source in a second chamber 74 for generating a sinusoidal signal at the Larmor frequency (in the example a one tone at $f_L$=$f_{B1}$=300 MHz). After low noise amplification and filtering, this signal is applied to a RF $T_x$-coil in a shielded & thermal controlled excitation chamber 75. This chamber also contains a Helmholtz type coil for generating a time-varying magnetic field $B_0(t)$. This is achieved by making use of a time-varying current i(t) having a frequency $f_{B0}$, originating from a voltage controlled current source VCCS present in a shielded & thermal controlled VCCS chamber 72. This voltage controlled oscillator uses the stable voltage and the reference oscillator signal generated in the first chamber 71. The magnetic field $B_1(t)$ generated by the RF $T_x$-coil and the magnetic field $B_0(t)$ generated by the Helmholtz type coil are oriented orthogonal to each other. A third coil, referred to as RF $R_x$-coil, is also present in the shielded & thermal controlled excitation chamber 73, for measuring the resultant magnetization signal originating from the volume containing the sample to be measured. The output of this RF $R_x$-coil is applied to a low noise amplification and filtering stage 75 and to a signal analyzer 76. In this experiment a spectrum analyzer which has typically a heterodyne receiver front end.

The sample is placed inside the $T_x$- and $R_x$-coil which are both placed together with the sample inside the Helmholtz type of coil all placed in the shielded & thermal controlled excitation chamber 73.

In the experiment, first a "Rienso® dilution A or Rie A" (quantity Fe 4500 µg diluted in 150 µl water), was placed in the excitation chamber, $f_{B1}$ was set to 300 MHz, $B_0$ was a sinusoidal waveform with an effective $B_0$=10.7 mT and $f_{B0}$=200 Hz. FIG. 6 shows the signal as can be seen on the signal analyzer 76, showing a number of peaks (also called side-bands) centered around 300 MHz at distances which are multiples of 200 Hz. The highest peak is representative of the Larmor frequency being applied to the volume by means of the first coil, while the other peaks are caused by the interaction with the paramagnetic nano-particle of the specimen under test.

Figure 7:
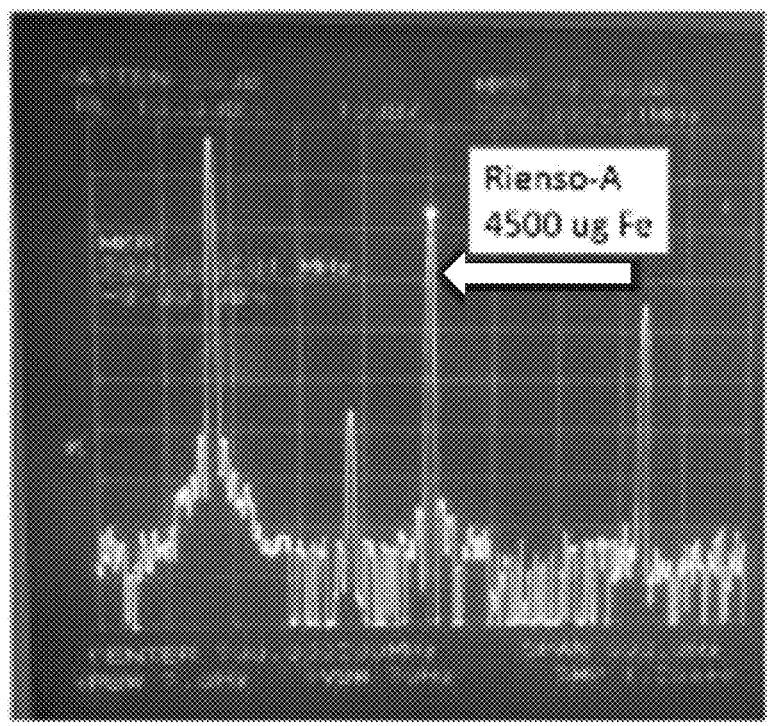
FIG. 7 shows an example of a frequency spectrum (measured with a spectrum analyzer having a heterodyne receiver front end) the spectrum being a spectrum of the measured signal, for a volume containing a "Rienso® dilution A, i.e. Rie A" sample containing 4500 μg (microgram) Fe, illustrating an embodiment of the present invention.

FIG. 7 shows the same spectrum as FIG. 6, but zoomed in at a frequency band from about (300 MHz−100 Hz) to about (300 MHz+500 Hz). The power of $f_{B1}$+$nf_{B0}$ with n=1 (indicated by the arrow) was measured, and is taken as a reference value for a mass of 4500 µg Fe (as present in Rie A). As described above, also the power at $f_{B1}$−$nf_{B0}$ with n=1 could have been used.

Figure 8:
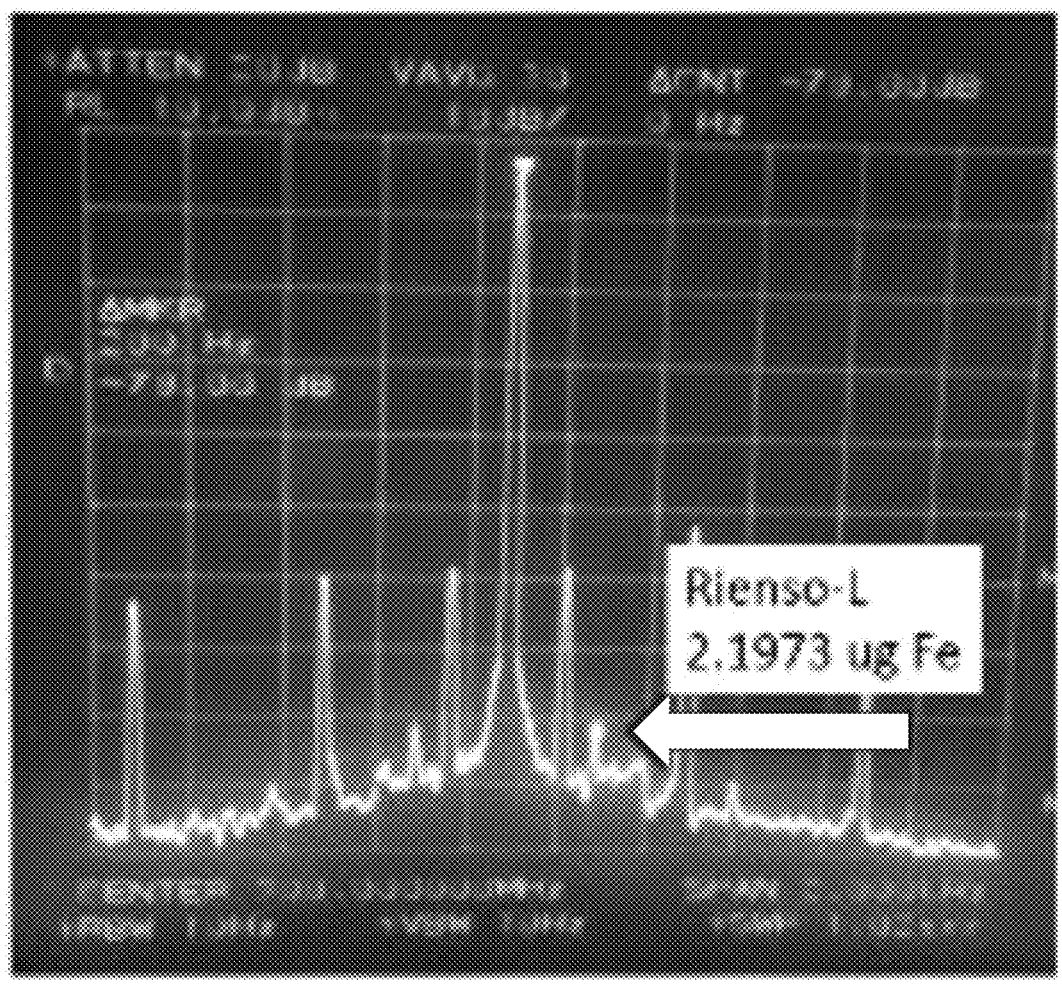
FIG. 8 shows an example of a frequency spectrum (measured with a spectrum analyzer, which has typ. a heterodyne receiver front end) of the measured signal, for a volume containing a "Rienso® dilution L, i.e. Rie L" sample containing 2.1973 μg (microgram) Fe.
Figure 9:
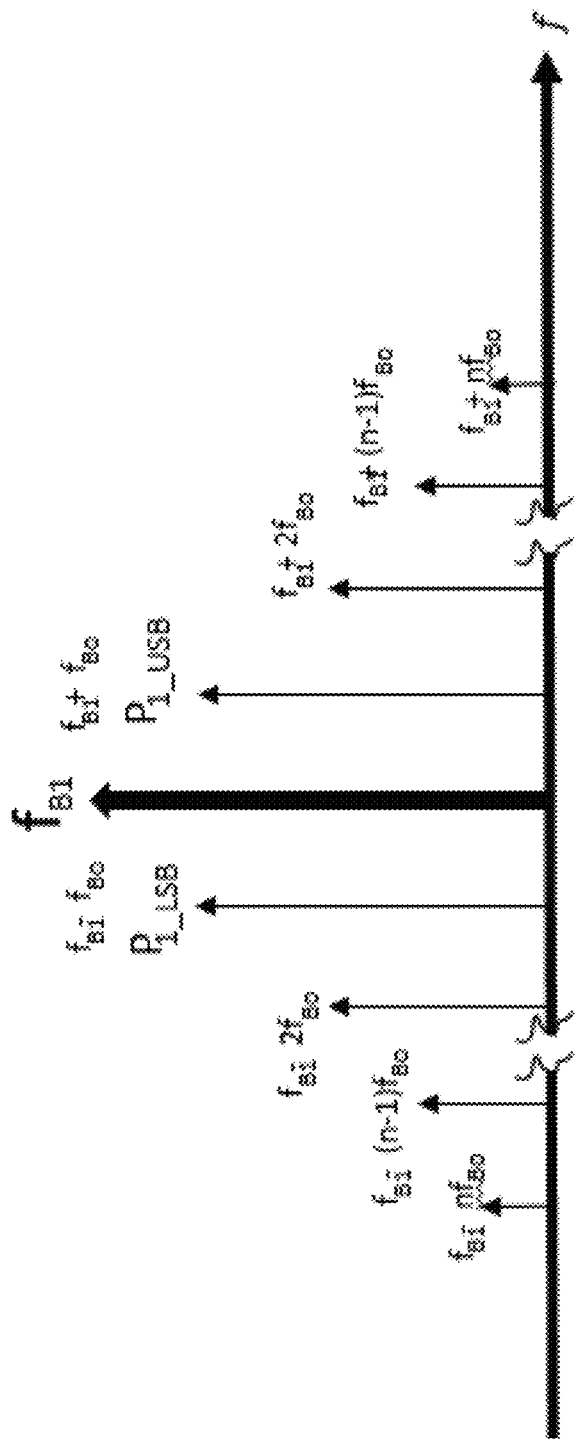
FIG. 9 illustrates the upper-sideband and the first lower-sideband of the frequency spectrum, around the Larmor frequency, $f_L=f_{B1}$.

After replacement of the "Rie A" sample by a "Rienso® dilution L or Rie L" sample (having 2.1973 µg Fe), and repeating the measurement, the spectrum as shown in FIG. 8 was obtained. (it is noted that the horizontal scale of FIG. 7 and FIG. 8 is not the same). The experiment was repeated also for other Rienso® samples, with different dilutions, the results of which are listed in Table 1 below.

As can be seen, each dilution sample was measured three times (indicated under heading Measured I, II, III). For each sample, the power of the first upper sideband (spectral component $P_{1\_USB}$) was measured (in dBm), and then converted to a voltage value.

TABLE 1

(measurement values)

| | Measured I [dBm] | Voltage [Vpp] | Measured II [dBm] | Voltage [Vpp] | Measured III [dBm] | Voltage [Vpp] |
|---|---|---|---|---|---|---|
| Rie A | −8.00 | 0.2518 | −8.00 | 0.2518 | −8.00 | 0.2518 |
| Rie B | −13.83 | 0.1287 | −13.83 | 0.1287 | −13.67 | 0.1311 |
| Rie C | −19.83 | 0.0645 | −19.67 | 0.0657 | −19.67 | 0.0657 |
| Rie D | −25.67 | 0.0329 | −25.50 | 0.0336 | −25.67 | 0.0329 |
| Rie E | −31.67 | 0.0165 | −31.50 | 0.0168 | −31.50 | 0.0168 |
| Rie F | −38.00 | 0.0080 | −38.00 | 0.0080 | −38.00 | 0.0080 |
| Rie G | −43.50 | 0.0042 | −43.67 | 0.0041 | −43.67 | 0.0041 |
| Rie H | −49.67 | 0.0021 | −49.83 | 0.0020 | −49.67 | 0.0021 |
| Rie I | −56.00 | 0.0010 | −56.17 | 0.0010 | −56.17 | 0.0010 |
| Rie J | −61.33 | 0.0005 | −61.00 | 0.006 | −60.83 | 0.0006 |
| Rie K | −68.00 | 0.0003 | −68.50 | 0.0002 | −67.00 | 0.0003 |
| Rie L | −72.33 | 0.0002 | −71.00 | 0.0002 | −72.56 | 0.0001 |

Then, as shown in Table 2, the average (indicated by µ) of the three measurements was calculated (both in logarithmic and linear scale), and the standard deviation (indicated by σ) was calculated. The value of the Rienso® sample A was taken as the reference value (meaning: power=0.2518 Vpp corresponds to mass=4500 µg Fe).

TABLE 2

| | M [dBm] | M [Vpp] | σ [Vpp] | Ref [µg] | Measured [µg] | σ [µg] |
|---|---|---|---|---|---|---|
| Rie A | −8.000 | 0.2518 | 0.00000 | 4500.0000 | — | — |
| Rie B | −13.777 | 0.1295 | 0.00138 | 2250.0000 | 2314.084 | 24.68674 |
| Rie C | −19.723 | 0.0653 | 0.00069 | 1125.0000 | 1166.933 | 12.37268 |
| Rie D | −25.613 | 0.0331 | 0.00038 | 562.5000 | 592.306 | 6.71496 |
| Rie E | −31.557 | 0.0167 | 0.00019 | 281.2500 | 298.799 | 3.36545 |
| Rie F | −38.000 | 0.0080 | 0.00000 | 140.6250 | 142.302 | 0.00000 |
| Rie G | −43.613 | 0.0042 | 0.00005 | 70.3125 | 74.567 | 0.84536 |
| Rie H | −49.723 | 0.0021 | 0.00002 | 35.1563 | 36.902 | 0.39126 |
| Rie I | −56.113 | 0.0010 | 0.00001 | 17.5781 | 17.683 | 0.20047 |
| Rie J | −61.053 | 0.0006 | 0.00002 | 8.7891 | 10.012 | 0.29182 |
| Rie K | −67.833 | 0.0003 | 0.00002 | 4.3945 | 4.587 | 0.40950 |
| Rie L | −71.963 | 0.0002 | 0.00002 | 2.1973 | 2.851 | 0.28401 |

In these measurements only the power of spectral component $P_{1\_USB}$ was measured (at $f_{B1}$+$nf_{B0}$ with n=1), but it would also have been possible to use the power of the spectral components at $f_{B1}$±$nf_{B0}$, with n=odd value.

For example, in order to determine the quantity of the Rie B sample, the magnetic fields of 200 Hz and 300 MHz described above would be applied again, and a measurement of the resultant magnetization would be performed, and the power $P_{1\_USB}$ (at $f_{B1}$+$nf_{B0}$ with n=1) of the spectrum of said magnetization would be determined, resulting in a value of Vpp=0.1295, and then the following calculation is used to determine the quantity of iron in the Rie B sample: 4500 µg×(0.1295/0.2518)=2314.084 µg, which is a good approximation of the actual mass of 2250 µg. The relative measurement error is (2314−2250)/2250=about 2.8%. The mass of the other samples is measured & calculated in the same manner. (It is noted that the above calculations are not optimized for accuracy, but only to demonstrate the feasibility of the method).

Figure 10:
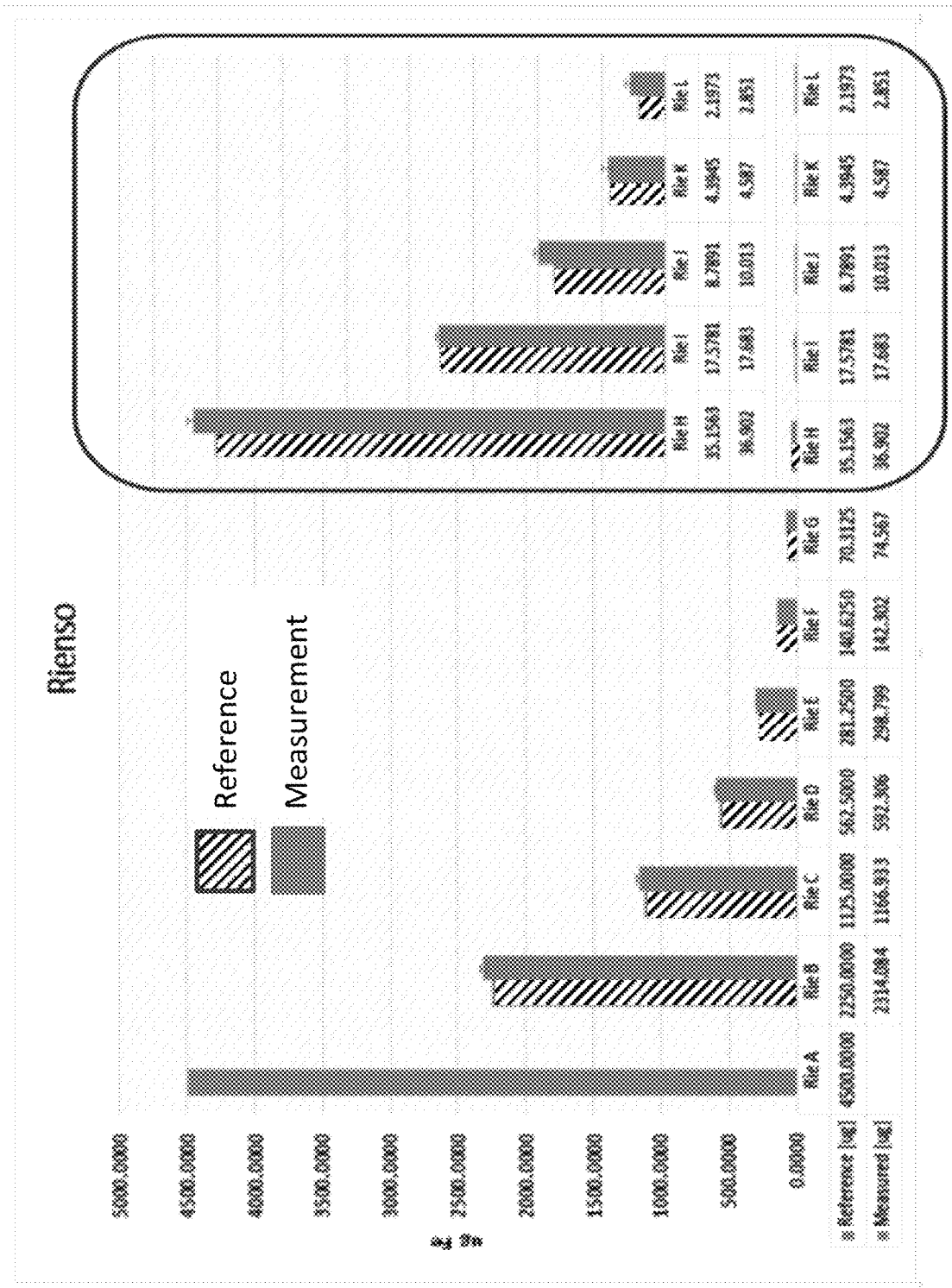
FIG. 10 shows the actual Fe content, and the content as determined by the method and/or system of the present invention, using a spectrum analyzer (left: normal scale, right: enlarged scale) for Rienso® sample A (4500 μg Fe) to Rienso® sample L (2.1973 μg Fe).

FIG. 10 gives a graphical representation of the actual Fe content and the measured Fe content by using embodiments of the present invention for Rie samples A to L. As can be seen, the results are quite accurate, over a relatively large range (from 4500 µg to 2.19 µg), which is more than three orders of magnitude.

Given the high sensitivity and large dynamic range, it is contemplated that this measurement technique can also be used for imaging e.g. organs of a patient, after administration of a liquid containing iron-oxide nanoparticles. In still another aspect, embodiments of the present invention also relate to computer-implemented methods for performing at least part of the methods as indicated above. The methods may be implemented in a computing system. They may be implemented as software, as hardware or as a combination thereof. Such methods may be adapted for being performed on computer in an automated and/or automatic way. In case of implementation or partly implementation as software, such software may be adapted to run on suitable computer or computer platform, based on one or more processors. The software may be adapted for use with any suitable operating system such as for example a Windows, Linux or any other operating system. The computing means may comprise a processing means or processor for processing data. According to some embodiments, the processing means or processor may be adapted for determining a quantity of magnetic particles, e.g. paramagnetic particles, enclosed in a volume according to any of the methods as described above. Besides a processor, the computing system furthermore may comprise a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of part or all of the standard steps of the methods as set out above and optionally of the optional steps as set out above. The obtained results may be outputted through an output means such as for example a plotter, printer, display or as output data in electronic format.

Further aspect of embodiments of the present invention encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

The invention claimed is:

1. A method of determining a quantity of magnetic particles enclosed in a volume, the method comprising the steps of:
    a) applying a first magnetic field to said volume for magnetizing said magnetic particles, where the magnetic field being a time-varying field having a magnitude and a first frequency;
    b) simultaneously applying to said volume a second magnetic field not parallel to the first magnetic field for causing precession of the magnetized particles, the second magnetic field being an RF field having a second frequency chosen substantially equal to the Larmor-frequency of electron spins of said magnetic particles when exposed to the first magnetic field;
    c) measuring the resultant magnetization originating from the volume by obtaining a voltage signal being representative for the resultant magnetization using a sensing element and determining a signal thereof, the resultant magnetization being modulated by the time-varying field;
    d) determining one or more frequency components of the resultant magnetization $f_{B1} \pm nf_{B0}$, n=1,3,5, . . . (i.e. n equals an odd value), the one or more frequency components comprising at least the component $f_{B1} \pm f_{B0}$, by performing a discrete Fourier transform on the signal, a power and/or voltage signal being representative for the resultant magnetization, and
    e) calculating a power and/or voltage of the one or more frequency components $f_{B1} \pm nf_{B0}$, n=1,3,5, . . . (i.e. n equals an odd value) of the resultant magnetization and determining from said power and/or voltage signal a quantity of the magnetic particles enclosed in the volume.

2. A system for determining a quantity of magnetic particles enclosed in a volume, the system comprising:
    a) a first signal source and a first magnetic field generator configured for generating and applying a first magnetic field to said volume for magnetizing said magnetic particles, the first magnetic field being a time-varying field having a first magnitude and a first frequency;
    b) a second signal source and a second magnetic field generator configured for simultaneously applying to said volume a second magnetic field not parallel with the first magnetic field, and having a frequency equal or close to the Larmor frequency of said magnetic particles for causing precession of the magnetized particles;
    c) a magnetization sensor configured for measuring the resultant magnetization, the resultant magnetization being modulated by the time varying field;
    d) a processor programmed for determining one or more frequency components of the resultant magnetization, the one or more frequency components comprising at least the frequency component $f_{B1} \pm f_{B0}$, and further programmed for calculating a power and/or voltage of the one or more frequency components of the resultant magnetization and for determining from said power and/or voltage a quantity of the magnetic particles enclosed in the volume.

3. A method according to claim 1, wherein determining the one or more frequency components $f_{B1} \pm nf_{B0}$, n=1, 3,5, . . . (i.e. n equals an odd value) of the resultant magnetization comprises determining a frequency spectrum of the resultant magnetization.

4. A method according to claim 1, wherein determining one or more frequency component ($f_{B1} \pm nf_{B0}$, with n=odd value i.e. n=1,3,5, . . .) comprises determining the one or more frequency components at a frequency equal to the second frequency minus the first frequency or at a frequency equal to the second frequency plus the first frequency.

5. A method according to claim 4, wherein determining from said power and/or voltage a quantity of the magnetic particles enclosed in the volume comprises determining a quantity based on a linear relationship between the power and/or voltage of said at least one spectral component and the mass of said magnetic particles.

6. A method according to claim 1, wherein determining from said power and/or voltage a quantity of the magnetic particles enclosed in the volume comprises comparing said power and/or voltage with a reference power and/or voltage determined for a known quantity of said magnetic particles.

7. A method according to claim 1, wherein the time varying first magnetic field is a periodic time varying field.

8. A method according to claim 1, wherein the time varying first magnetic field has a sinusoidal waveform.

9. A method of imaging an object, the method comprising applying a method of determining a quantity of magnetic particles in a given volume according to claim 1 at a plurality of positions in the object, the determining being applied after administration of a dilution comprising said magnetic particles to an object.

10. The method of claim 1, wherein the frequency of the second magnetic field is at least 50 MHz.

11. A system according to claim 2, wherein the processor furthermore is programmed for determining the one or more frequency components at least at a frequency equal to the second frequency minus the first frequency or at a frequency equal to the second frequency plus the first frequency.

12. A system according to claim 2, the system furthermore comprising a memory for storing a reference power and/or voltage determined for a known quantity of said magnetic particles and the processor being programmed for comparing the determined power or voltage with the reference power and/or voltage for determining a quantity of the magnetic particles enclosed in the volume.

13. A system according to claim 2 wherein the first signal source is adapted for generating a periodically varying first magnetic field with a frequency in a range from almost several Hz to 100 kHz.

14. A system according to claim 2, wherein the processor comprises a calculator for calculating a frequency spectrum of the resultant magnetization.

15. A system according to claim 14, wherein the calculator for calculating a frequency spectrum comprises a processor for performing a (discrete) Fourier-transform.

16. A system according to claim 14, wherein the processor comprises a signal analyzer for determining a power and/or voltage of at least one frequency component in the frequency spectrum of the resultant magnetization.

17. The method of claim 2, wherein the frequency of the second magnetic field is at least 50 MHz.

* * * * *